(12) United States Patent
LaVon et al.

(10) Patent No.: US 10,441,476 B2
(45) Date of Patent: Oct. 15, 2019

(54) CONVERTING LINES AND METHODS FOR FABRICATING BOTH TAPED AND PANT DIAPERS COMPRISING SUBSTANTIALLY IDENTICAL CHASSIS

(71) Applicant: The Procter & Gamble Company, Cincinnati, OH (US)

(72) Inventors: Gary Dean LaVon, Liberty Township, OH (US); Michael Gary Nease, Fairfield, OH (US); Gene Xiaoqing Huang, Mason, OH (US); Jacob Alan Barnhorst, Deefield Township, OH (US); Masaharu Nishikawa, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 4 days.

(21) Appl. No.: 14/953,471

(22) Filed: Nov. 30, 2015

(65) Prior Publication Data
US 2016/0136004 A1    May 19, 2016

Related U.S. Application Data

(63) Continuation of application No. 13/372,940, filed on Feb. 14, 2012, now Pat. No. 9,226,861, which is a
(Continued)

(51) Int. Cl.
*A61F 13/15*    (2006.01)
*A61F 13/49*    (2006.01)
(Continued)

(52) U.S. Cl.
CPC ........ *A61F 13/15772* (2013.01); *A61F 13/49* (2013.01); *A61F 13/496* (2013.01);
(Continued)

(58) Field of Classification Search
CPC ............ A61F 13/55105; A61F 13/5519; A61F 13/15772; A61F 13/49; A61F 13/49009; A61F 13/496; A61F 13/539; A61F 13/5633; A61F 13/622; A61F 13/64; A61F 2013/530481; A61F 2013/5395
(Continued)

(56) References Cited

U.S. PATENT DOCUMENTS 2,075,189 A    3/1937    Galligan et al.
3,025,199 A    3/1962    Harwood
(Continued)

FOREIGN PATENT DOCUMENTS

EP    0 589 859 A1    3/1994
JP    03-231660        10/1991
(Continued)

OTHER PUBLICATIONS

PCT International Search Report and Written Opinion dated Jul. 4, 2011, 4 pages.
(Continued)

*Primary Examiner* — Jacqueline F Stephens
(74) *Attorney, Agent, or Firm* — Richard L. Alexander

(57) ABSTRACT

The present disclosure relates to taped and pant articles comprising substantially identical chassis.

26 Claims, 27 Drawing Sheets

Related U.S. Application Data continuation-in-part of application No. 13/371,919, filed on Feb. 13, 2012, now abandoned, which is a continuation-in-part of application No. 13/074,058, filed on Mar. 29, 2011, now abandoned.

(60) Provisional application No. 61/322,359, filed on Apr. 9, 2010.

(51) Int. Cl.
| | |
|---|---|
| *A61F 13/496* | (2006.01) |
| *A61F 13/551* | (2006.01) |
| *A61F 13/539* | (2006.01) |
| *A61F 13/56* | (2006.01) |
| *A61F 13/62* | (2006.01) |
| *A61F 13/64* | (2006.01) |
| *A61F 13/53* | (2006.01) |

(52) U.S. Cl.
CPC ...... *A61F 13/49009* (2013.01); *A61F 13/539* (2013.01); *A61F 13/55105* (2013.01); *A61F 13/5633* (2013.01); *A61F 13/622* (2013.01); *A61F 13/64* (2013.01); *A61F 2013/5395* (2013.01); *A61F 2013/530481* (2013.01)

(58) Field of Classification Search
USPC .................. 604/385.02, 385.01; 206/438
See application file for complete search history.

(56) References Cited

U.S. PATENT DOCUMENTS

| | | | |
|---|---|---|---|
| 3,848,594 A | 11/1974 | Buell et al. | |
| 3,860,003 A | 1/1975 | Buell | |
| 4,107,364 A | 8/1978 | Sisson | |
| 4,209,563 A | 6/1980 | Sisson | |
| 4,515,595 A | 5/1985 | Kievit et al. | |
| 4,610,678 A | 9/1986 | Weisman et al. | |
| 4,662,875 A | 5/1987 | Hirotsu et al. | |
| 4,673,402 A | 6/1987 | Weisman et al. | |
| 4,695,278 A | 9/1987 | Lawson | |
| 4,704,115 A | 11/1987 | Buell | |
| 4,795,454 A | 1/1989 | Dragoo | |
| 4,834,735 A | 5/1989 | Alemany et al. | |
| 4,834,741 A | 5/1989 | Sabee | |
| 4,846,815 A | 7/1989 | Scripps | |
| 4,888,231 A | 12/1989 | Angstadt | |
| 4,894,060 A | 1/1990 | Nestegard | |
| 4,909,803 A | 3/1990 | Aziz et al. | |
| 4,940,464 A * | 7/1990 | Van Gompel | A61F 13/539 604/385.22 |
| 4,946,527 A | 8/1990 | Battrell | |
| 5,092,861 A | 3/1992 | Nomura et al. | |
| 5,151,092 A | 9/1992 | Buell et al. | |
| 5,167,897 A | 12/1992 | Weber et al. | |
| 5,221,274 A | 6/1993 | Buell et al. | |
| 5,246,433 A | 9/1993 | Hasse et al. | |
| 5,330,458 A | 7/1994 | Buell et al. | |
| 5,360,420 A | 11/1994 | Cook et al. | |
| 5,366,782 A | 11/1994 | Curro et al. | |
| 5,518,801 A | 5/1996 | Chappell et al. | |
| 5,562,646 A | 10/1996 | Goldman et al. | |
| 5,569,234 A | 10/1996 | Buell et al. | |
| 5,599,335 A | 2/1997 | Goldman et al. | |
| 5,607,537 A | 3/1997 | Johnson et al. | |
| 5,622,589 A | 4/1997 | Johnson et al. | |
| 5,628,097 A | 5/1997 | Benson et al. | |
| 5,643,588 A | 7/1997 | Roe et al. | |
| 5,662,638 A | 9/1997 | Johnson et al. | |
| 5,669,894 A | 9/1997 | Goldman et al. | |
| 5,674,216 A | 10/1997 | Buell et al. | |
| 5,702,551 A | 12/1997 | Huber et al. | |
| 5,735,840 A | 4/1998 | Kline et al. | |
| 5,772,825 A | 6/1998 | Schmitz | |
| 5,779,831 A | 7/1998 | Schmitz | |
| 5,876,391 A | 3/1999 | Roe | |
| 5,897,545 A | 4/1999 | Kline et al. | |
| 5,916,661 A | 6/1999 | Benson et al. | |
| 5,928,212 A | 7/1999 | Kline et al. | |
| 5,957,908 A | 9/1999 | Kline et al. | |
| 5,968,025 A | 10/1999 | Roe et al. | |
| 5,971,153 A | 10/1999 | Bauer et al. | |
| 6,042,673 A | 3/2000 | Johnson et al. | |
| 6,079,562 A | 6/2000 | Bauer et al. | |
| 6,107,537 A | 8/2000 | Elder et al. | |
| 6,107,539 A | 8/2000 | Palumbo et al. | |
| 6,118,041 A | 9/2000 | Roe et al. | |
| 6,120,487 A | 9/2000 | Ashton | |
| 6,120,489 A | 9/2000 | Johnson et al. | |
| 6,153,209 A | 11/2000 | Vega et al. | |
| 6,251,097 B1 | 6/2001 | Kline et al. | |
| 6,410,129 B2 | 6/2002 | Zhang et al. | |
| 6,426,444 B2 | 7/2002 | Roe et al. | |
| 6,432,098 B1 | 8/2002 | Kline et al. | |
| 6,545,197 B1 | 4/2003 | Muller et al. | |
| 6,586,652 B1 | 7/2003 | Roe et al. | |
| 6,617,016 B2 | 9/2003 | Zhang et al. | |
| 6,627,787 B1 | 9/2003 | Roe et al. | |
| 6,669,618 B2 | 12/2003 | Reising et al. | |
| 6,723,035 B2 | 4/2004 | Franklin et al. | |
| 6,726,792 B1 | 4/2004 | Johnson et al. | |
| 6,763,944 B2 | 7/2004 | Ronn et al. | |
| 6,776,316 B2 | 8/2004 | VanEperen et al. | |
| 6,790,798 B1 | 9/2004 | Suzuki et al. | |
| 6,825,393 B2 | 11/2004 | Roe et al. | |
| 6,861,571 B1 | 3/2005 | Roe et al. | |
| 6,971,153 B2 | 12/2005 | Tokizawa et al. | |
| 7,028,841 B2 | 4/2006 | Otsubo | |
| 7,048,124 B2 | 5/2006 | Osterdahl et al. | |
| 7,059,474 B2 | 6/2006 | Tippey | |
| 7,222,732 B2 | 5/2007 | Ronn et al. | |
| 7,967,805 B2 | 6/2011 | Ohnishi et al. | |
| 8,079,994 B2 | 12/2011 | Richlen et al. | |
| 8,092,438 B2 | 1/2012 | Betts et al. | |
| 8,321,049 B2 | 11/2012 | Healey et al. | |
| 8,439,814 B2 | 5/2013 | Piantoni et al. | |
| 8,585,666 B2 | 11/2013 | Weisman et al. | |
| 9,226,861 B2 | 1/2016 | LaVon et al. | |
| 2002/0072723 A1 | 6/2002 | Ronn et al. | |
| 2003/0088220 A1 | 5/2003 | Molander et al. | |
| 2003/0233082 A1 | 12/2003 | Kline et al. | |
| 2004/0097895 A1 | 5/2004 | Busam et al. | |
| 2004/0097897 A1 | 5/2004 | Ronn et al. | |
| 2004/0158212 A1 | 8/2004 | Ponomarenko et al. | |
| 2005/0130821 A1 | 6/2005 | Reising et al. | |
| 2005/0215970 A1 | 9/2005 | Kline et al. | |
| 2005/0215971 A1 | 9/2005 | Roe et al. | |
| 2005/0222550 A1 | 10/2005 | Mitsui et al. | |
| 2005/0234419 A1 | 10/2005 | Kline et al. | |
| 2006/0030831 A1 * | 2/2006 | Matsuda | A61F 13/15699 604/392 |
| 2007/0074381 A1 | 4/2007 | Raycheck et al. | |
| 2007/0078426 A1 | 4/2007 | Kline et al. | |
| 2007/0078427 A1 | 4/2007 | Raycheck et al. | |
| 2007/0093769 A1 | 4/2007 | Kline et al. | |
| 2007/0213678 A1 | 9/2007 | Thorson et al. | |
| 2008/0021747 A1 | 1/2008 | Moeller et al. | |
| 2008/0082071 A1 * | 4/2008 | Bryant | A61F 13/51496 604/385.02 |
| 2008/0107861 A1 | 5/2008 | Dalal et al. | |
| 2009/0094941 A1 | 4/2009 | Burns, Jr. et al. | |
| 2009/0098995 A1 | 4/2009 | Burns, Jr. et al. | |
| 2009/0264851 A1 | 10/2009 | Richlen et al. | |
| 2009/0266733 A1 | 10/2009 | Betts et al. | |
| 2009/0312730 A1 | 12/2009 | LaVon et al. | |
| 2011/0046772 A1 | 2/2011 | Healey et al. | |
| 2011/0077609 A1 | 3/2011 | Kuwano | |
| 2011/0178490 A1 | 7/2011 | LaVon et al. | |
| 2011/0247199 A1 | 10/2011 | LaVon | |
| 2011/0272315 A1 | 11/2011 | Dixon | |
| 2012/0246915 A1 | 10/2012 | LaVon et al. | |
| 2013/0018351 A1 | 1/2013 | Desai | |
| 2013/0072887 A1 | 3/2013 | LaVon et al. | |

(56) References Cited

U.S. PATENT DOCUMENTS

| | | |
|---|---|---|
| 2013/0110068 A1 | 5/2013 | Nelson et al. |
| 2013/0211355 A1 | 8/2013 | Nishikawa et al. |
| 2013/0211356 A1 | 8/2013 | Nishikawa et al. |
| 2013/0211357 A1 | 8/2013 | Nishikawa et al. |
| 2013/0244355 A1 | 9/2013 | Chen et al. |
| 2016/0136004 A1 | 5/2016 | LaVon et al. |

FOREIGN PATENT DOCUMENTS

| | | |
|---|---|---|
| JP | 2003-180751 | 7/2003 |
| JP | 2004-188225 | 7/2004 |
| JP | 2005-126119 | 5/2005 |
| JP | 2008-289640 | 12/2008 |
| WO | WO 01/056524 A1 | 8/2001 |
| WO | WO-2007146153 | 12/2007 |
| WO | WO-2011/126828 | 10/2011 |

OTHER PUBLICATIONS

PCT International Search Report and Written Opinion dated Jul. 5, 2011, 11 pages.
All Office Actions, Responses, Claims for U.S. Appl. No. 13/764,945.
All Office Actions, Responses, Claims for U.S. Appl. No. 13/764,954.
All Office Actions, Responses, Claims for U.S. Appl. No. 13/764,964.
All Office Actions, Responses, Claims for U.S. Appl. No. 13/074,058.
All Office Actions, Responses, Claims for U.S. Appl. No. 13/371,919.
All Office Actions, Responses, Claims for U.S. Appl. No. 13/372,940.
Non-Final Rejection for U.S. Appl. No. 13/764,945, dated Oct. 24, 2014.
Non-Final Rejection for U.S. Appl. No. 13/764,954, dated Sep. 18, 2014.
Non-Final Rejection for U.S. Appl. No. 13/764,964, dated Oct. 10, 2014.
Non-Final Rejection for U.S. Appl. No. 13/074,058, dated Mar. 7, 2013.
Amendment for U.S. Appl. No. 13/074,058, dated Jun. 7, 2013.
Non-Final Rejection for U.S. Appl. No. 13/074,058, dated Aug. 15, 2013.
Amendment for U.S. Appl. No. 13/074,058, dated Nov. 15, 2013.
Final Rejection for U.S. Appl. No. 13/074,058, dated Dec. 4, 2013.
RCE and Amendment for U.S. Appl. No. 13/074,058, dated Mar. 4, 2014.
Non-Final Rejection for U.S. Appl. No. 13/074,058, dated Apr. 25, 2014.
Amendment for U.S. Appl. No. 13/074,058, dated Jul. 23, 2014.

* cited by examiner

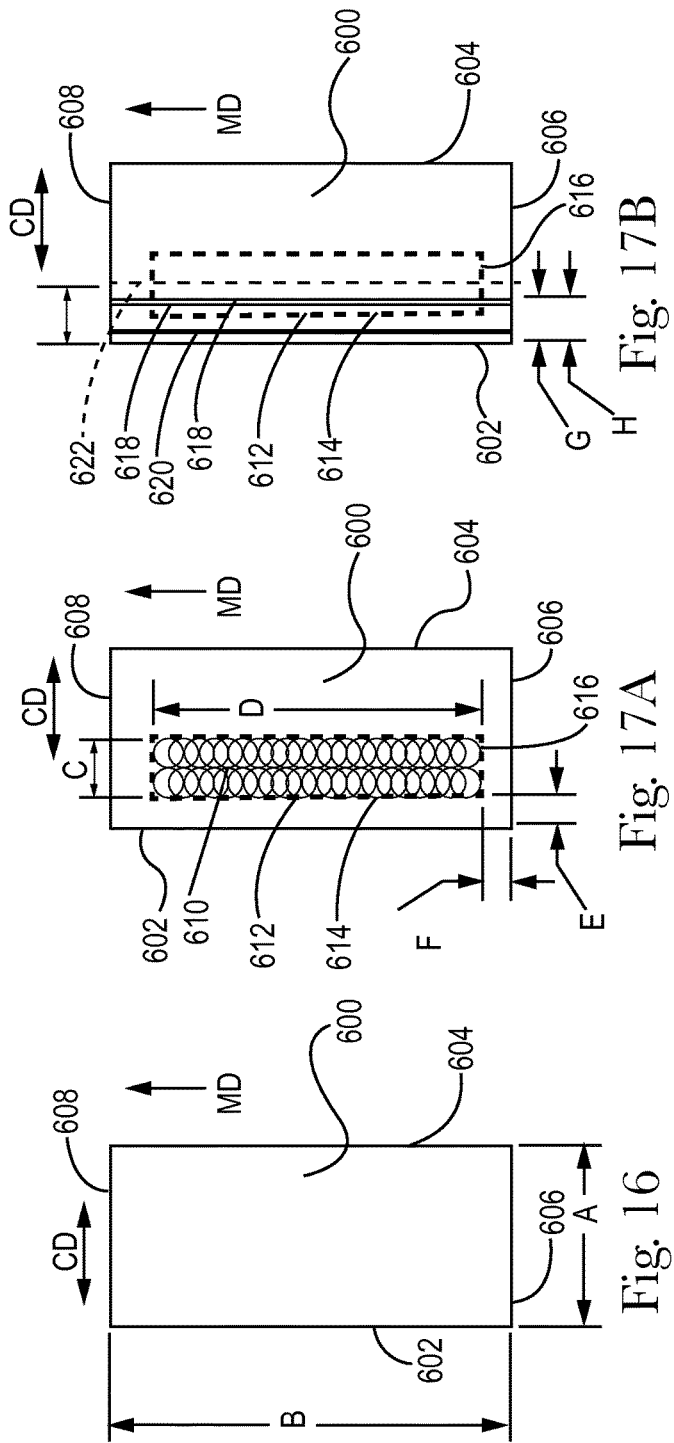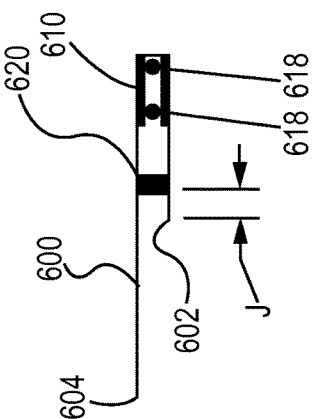

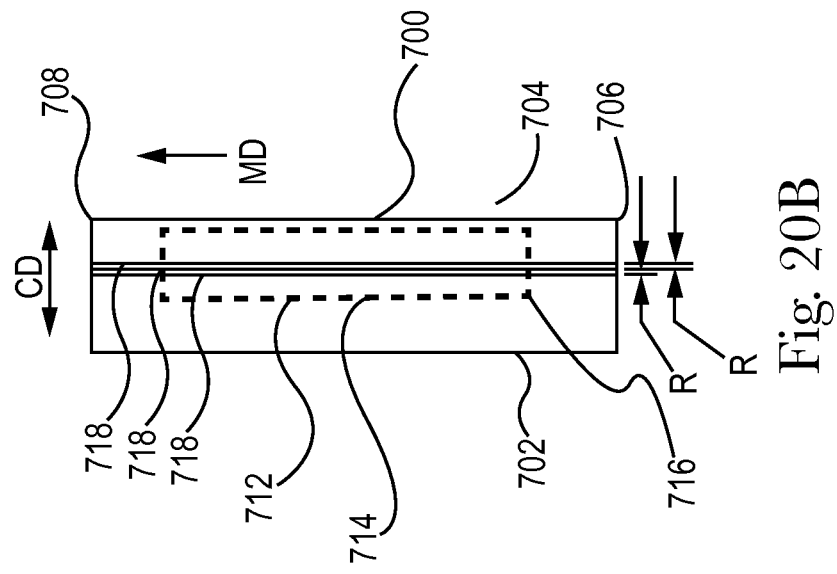
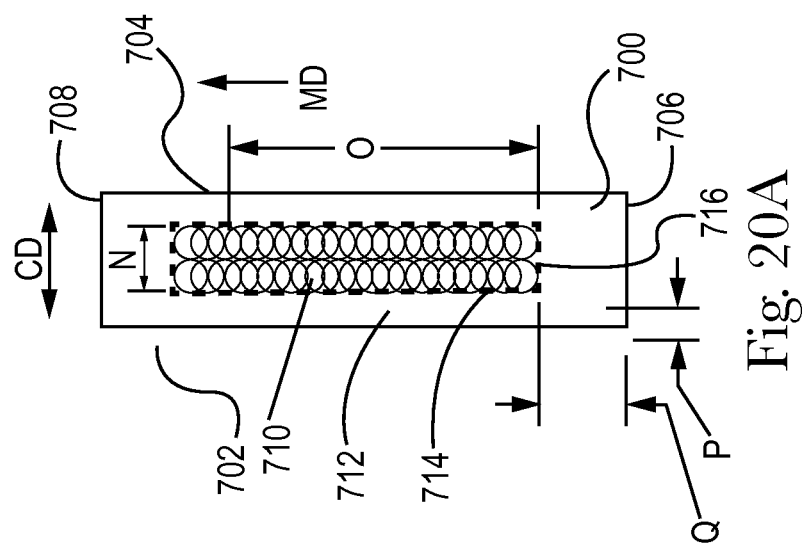
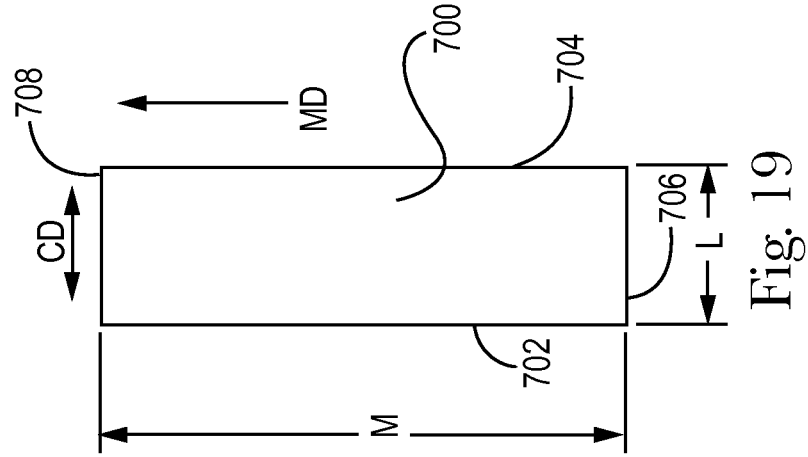

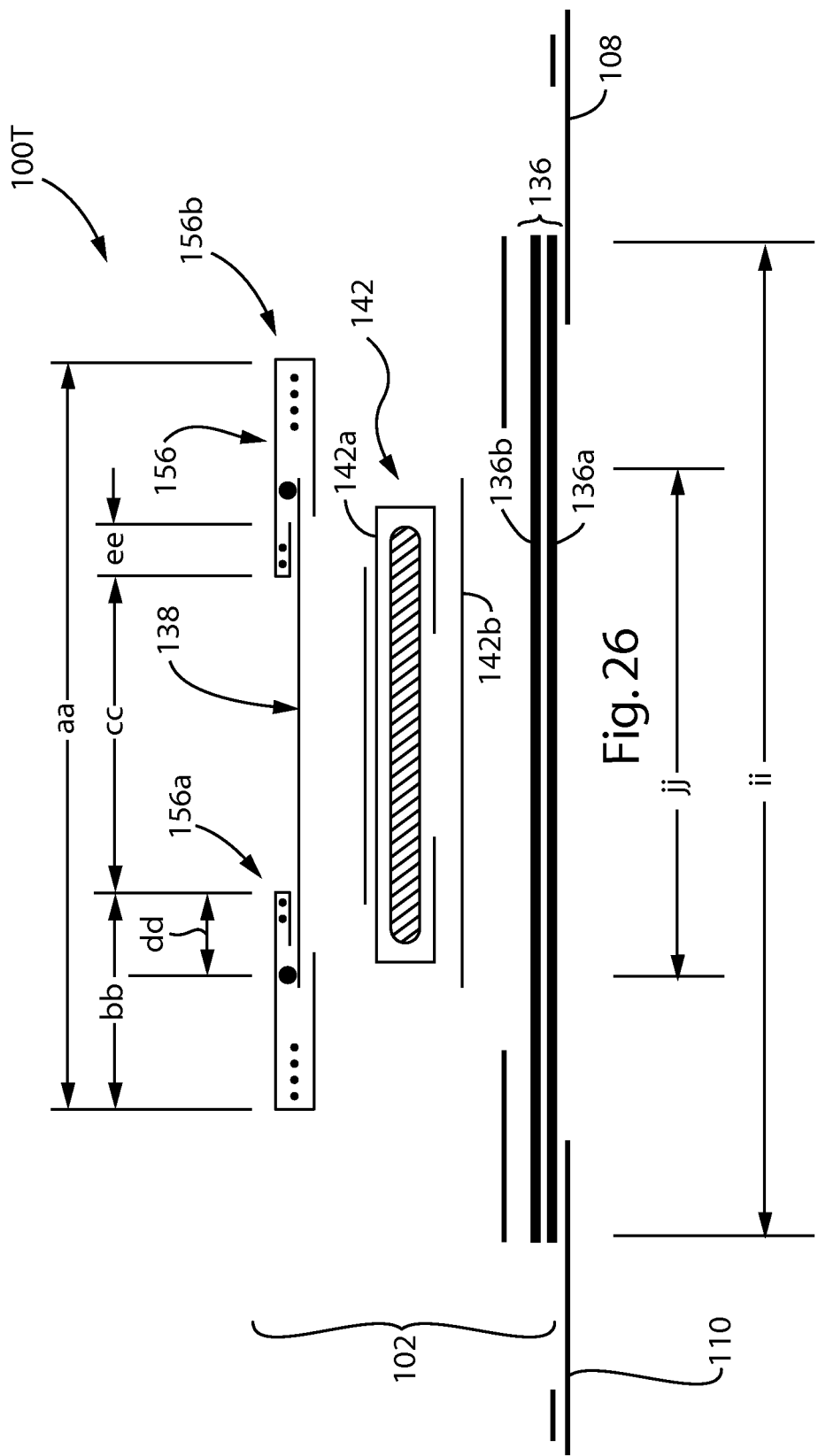

CONVERTING LINES AND METHODS FOR FABRICATING BOTH TAPED AND PANT DIAPERS COMPRISING SUBSTANTIALLY IDENTICAL CHASSIS

CROSS REFERENCE TO RELATED APPLICATIONS

This application is a continuation of U.S. application Ser. No. 13/372,940, filed Feb. 14, 2012, which is a continuation-in-part of U.S. application Ser. No. 13/371,919, filed on Feb. 13, 2012, which is a continuation-in-part of U.S. application Ser. No. 13/074,058, filed on Mar. 29, 2011, which claims the benefit of U.S. Provisional Application No. 61/322,359, filed on Apr. 9, 2010, the substances of which are hereby incorporated by reference.

FIELD OF THE INVENTION

The present disclosure relates to converting lines for manufacturing disposable taped and pant absorbent articles.

BACKGROUND OF THE INVENTION

Disposable, reusable and durable products such as diapers, adult incontinence articles, feminine hygiene tampons, sanitary napkins, underpants, shirts, shorts, swimsuits, gowns, pants, coats, gloves, scarves, surgical drapes, bibs, blankets, sheets, pillow cases, etc. may be manufactured on high speed converting lines. Such converting lines may utilize a web-based carrier to which many source materials, whether in a continuous web or discrete pieces, are processed and/or attached to the web to create a finished product.

Although a converting line may allow for high speed production of a specific type of absorbent article, some converting lines may be inflexible in that line changes that would be required to accommodate the production of different types of products would be so time consuming and/or expensive as to be economically impractical. For instance, some converting lines are custom designed and built to make specific products within a narrow range of parameters and operating conditions. For example, converting lines may be custom designed to make only taped diapers, whereas other converting lines may be custom designed to make only pant diapers. Thus, such custom converting lines may be used to produce particular types of diapers, e.g. taped or pant, in certain markets in an effort to provide a good match with business needs. However, the inflexibility of such converting lines to produce more than one type of product can place unwanted limitations on a manufacturer's ability to provide multiple product offerings in some markets.

In markets having consumer demand for both taped diapers and pant diapers, a manufacturer may be required to have separate converting lines, each custom designed to produce one of the two products. However, consumer demand of one or both of the products may not be high enough to justify the manufacturer's cost of having separate converting lines dedicated to each of the product types. For example, if the demand for pant diapers in a particular market is not high enough to justify the cost of a converting line that produces only pant diapers, the manufacture may decide not to offer pant diapers in the market. In such markets, the flexibility to produce both products on the same converting line and therefore produce the proper mix of product to meet the market needs may provide the most efficient and cost effective approach.

In some markets, disposable taped diapers are used for infants from birth to a point when infants begin potty training. As an alternative to taped diapers, disposable pant diapers may be desirable and useful products for children in the potty training stage. In yet other instances, the use of pant diapers may start at an earlier age than ages typically associated with potty training, and therefore, pant diapers may be used more like a taped diaper than a training pant. One difference between taped diapers and pant diapers is how the two products are delivered from the manufacturer to the consumer, i.e. packaged. In particular, both taped diapers and pant diapers can generally include an absorbent chassis having a liquid impervious outer cover, a liquid pervious body-side liner, and an absorbent structure. However, a taped diaper may not have a closed initial waist opening circumference or leg openings prior to being removed from the package, whereas the absorbent chassis and/or the side panels (when present) of a pant diaper may be pre-closed to form an initial waist opening circumference and two leg openings. Since the percentage of users that prefer taped diapers versus a pant style, pull-on, diaper varies market to market it may be advantageous for a manufacturer to have the flexibility to produce both a taped diaper and a pant, pull-on, diaper on the same converting line in any desired ratio to meet the needs to the intended market.

Some attempts have been made to create converting lines that are capable of producing more than one type of diaper, such as disclosed in U.S. Patent Publication No. 2007/0213678A1. However, such converting lines represent a mere conglomeration or assembly of different converting lines designed to build specific types of diapers. These converting lines may utilize a relatively low number of the same processes and machinery when producing different types of diapers. Thus, a relatively large number of different processes and machinery in such converting lines are either turned-on or turned-off depending on what type of diaper is being produced. As such, a converting line that includes a relatively large number of processes that may not be used when producing different types of diapers may result in large capital costs, require large amounts of space and require additional maintenance.

Thus, there remains a need to develop a converting line that is capable of producing different types of diapers while at the same time utilizing a substantial number of the same processes and machinery to produce either the range of diaper types resulting in greater efficiency and lower overall cost.

BRIEF DESCRIPTION OF THE DRAWINGS

FIG. 16 is a top plan view of a nonwoven specimen for an inner cuff.

FIG. 17A is the nonwoven specimen of FIG. 16 including a glue pattern.

FIG. 17B is the nonwoven specimen of FIG. 17A including elastic strands.

FIG. 18 is a cross-sectional view of an inner cuff with a continuous hem bond.

FIG. 19 is a top plan view of a nonwoven specimen for an outer cuff.

FIG. 20A is the nonwoven specimen of FIG. 19 including a glue pattern.

FIG. 20B is the nonwoven specimen of FIG. 20A including elastic strands.

FIG. 26 is a schematic cross section view of an exemplary absorbent article, suitable in one embodiment of the invention.

DETAILED DESCRIPTION OF THE INVENTION

Figure 1:
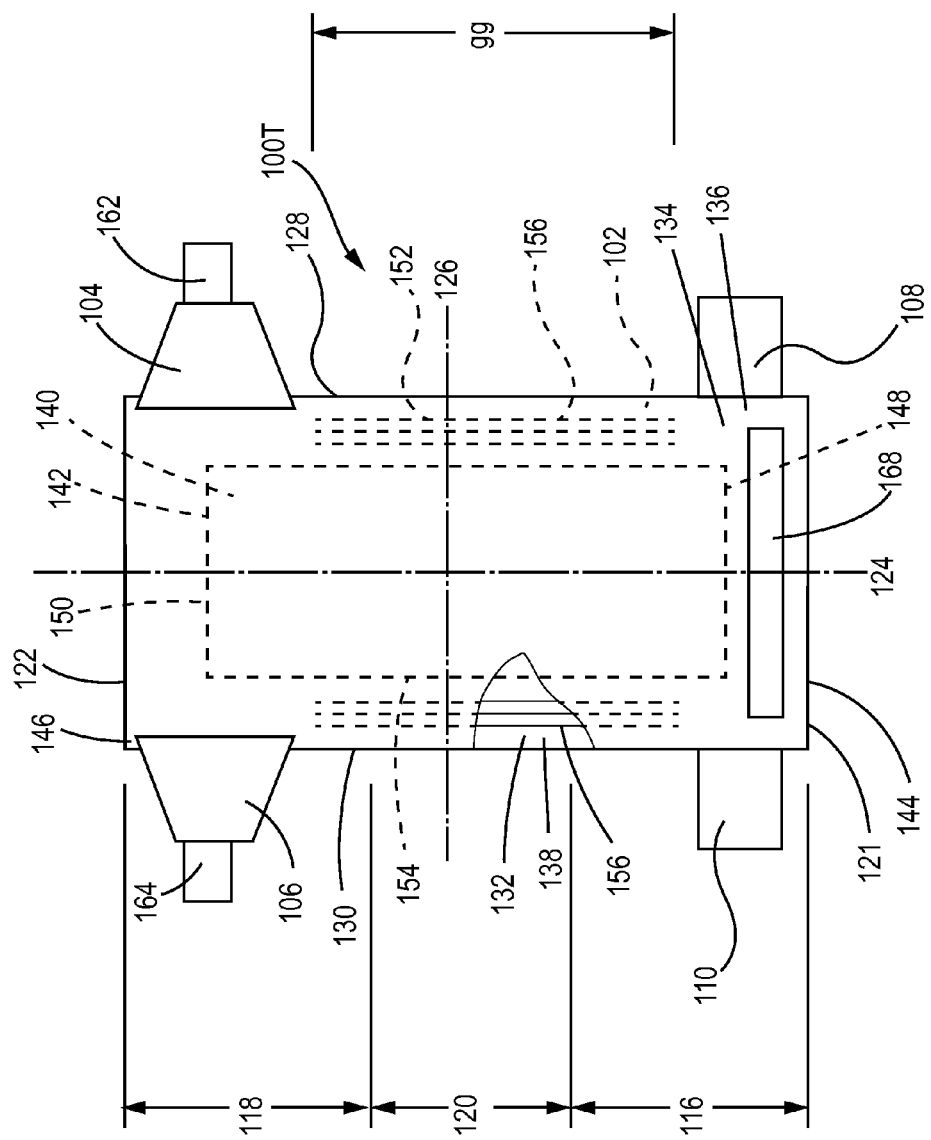
FIG. 1 is a partially cut away plan view of a taped diaper with the portion of the diaper that faces away from a wearer oriented towards the viewer.

The following term explanations may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

The term "disposed" is used herein to mean that an element(s) is formed (joined and positioned) in a particular place or position as a macro-unitary structure with other elements or as a separate element joined to another element.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

The term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) is used herein to refer to the primary direction of material flow through a process. In various manufacturing and converting processes, such as a bi-fold process, it may be possible to have more than one machine direction when an article is undergoing simultaneous processes. In other words, a manufacturing line may have an overall machine direction, but an article may travel in directions other than the overall machine direction as it passes through various processes along the manufacturing line. For example, an article having a trailing end portion and a leading end portion, each portion being attached to the surface of a different roll and/or conveyor, may travel in two different directions simultaneously. In this example, both directions of travel may be considered the machine direction. The term "cross direction" (CD) is used herein to refer to a direction that is generally perpendicular to the machine direction.

The term "transformation" refers herein to a change or activity resulting in a change in a web, layer, article, plurality of articles, material or portions thereof with regard to the thickness, length, width, shape, relative position, texture, color, tackiness, etc. Transformations are: fiberization, core component mixing, core formation/deposition, slitting, cutting, notching, shaping, perforation, die cutting, trimming, thermal bonding, ultrasonic bonding, pressure bonding, radio frequency bonding, seaming, adhesive application, cohesive application, lotion application, folding, bi-folding, tucking, spacing, MD positioning, CD positioning, registration, activation, compression, nipping, calendaring, substrate combining, component combining, web combining, elastic tensioning, fastening element pre-fastening, product stacking, and packaging.

The term "transformation mechanism" refers herein to an apparatus adapted to produce a transformation.

The term "taped diaper" (also referred to as "open diaper") refers to disposable absorbent articles having an initial front waist region and an initial back waist region that are not fastened, pre-fastened, or connected to each other as packaged, prior to being applied to the wearer. A taped diaper may be folded about the lateral centerline with the interior of one waist region in surface to surface contact with the interior of the opposing waist region without fastening or joining the waist regions together. Example taped diapers are disclosed in various suitable configurations are disclosed in U.S. Pat. Nos. 5,167,897, 5,360,420, 5,599,335, 5,643,588, 5,674,216, 5,702,551, 5,968,025, 6,107,537, 6,118,041, 6,153,209, 6,410,129, 6,426,444, 6,586,652, 6,627,787, 6,617,016, 6,825,393, and 6,861,571.

The term "pant" (also referred to as "training pant", "pre-closed diaper", "diaper-pant", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed). Example diaper pants in various configurations are disclosed in U.S. Pat. Nos. 5,246,433; 5,569,234; 6,120,487; 6,120,489; 4,940,464; 5,092,861; 5,897,545; 5,957,908; and U.S. Patent Publication No. 2003/0233082.

The term "initial waist opening circumference" refers herein to the circumference of the waist opening at the time the pant is placed in the package and subsequently when it is removed from the package by the consumer.

The present disclosure relates to converting lines for manufacturing absorbent articles, and in particular, converting lines that are reconfigurable to produce both taped diapers and pant diapers. As discussed in more detail below, an absorbent article converting line may include a combination of converting mechanisms that advance substrates and component materials through a manufacturing process. While advancing in the machine direction MD through the converting line, substrates may be modified and/or combined with the other substrates and/or discrete components to create a continuous length of absorbent articles. Various substrates can be used to construct various components of the absorbent articles, such as backsheets, topsheets, and absorbent cores. Exemplary descriptions of absorbent article components with respect to both taped diapers and pant diapers are provided below. At a downstream portion of the converting process, the continuous length of absorbent articles may be subjected to a final knife and cut to create separate and discrete absorbent articles. In addition, defective articles may be removed from the process by a rejection system. Articles that are not deemed to be defective may be subject to further processing steps, such as folding and packaging.

Aspects of the apparatuses and methods according to the present disclosure relate to a converting apparatus for the fabrication of absorbent articles and adapted to operate in a first configuration and a second configuration. As discussed in more detail below, the converting apparatus includes transformation mechanisms adapted to produce a series of transformations. In the first configuration, a first plurality of the transformation mechanisms are arranged to produce a plurality of taped diapers, wherein the first plurality of the transformation mechanisms produce a first number of transformations. In the second configuration, a second plurality of the transformation mechanisms are arranged to produce a plurality of pant diapers, wherein the second plurality of the transformation mechanisms produce a second number of transformations. The converting apparatus is configured with relatively high flexibility in changing between the first and second configurations, because greater than 70% of the second number of transformations are the same as the first number of transformations resulting in greater efficiency and equipment utilization.

In another form, the first configuration may include a first plurality of transformation mechanisms adapted to produce a first number of transformations, wherein the first number of transformations may be carried out in a first sequence advancing from a first transformation to a last transformation. In addition, the second configuration may include a second plurality of the transformation mechanisms adapted to produce a second number of transformations. The second number of transformations may be carried out in a second sequence advancing from a first transformation to a last transformation. Again, the converting apparatus is configured with relatively high flexibility in changing between the first and second configurations, because 70% of the second number of transformations is carried out in an identical order as the first number of transformations with respect to one or more of preceding transformations in the first number of transformations.

Figure 1A:
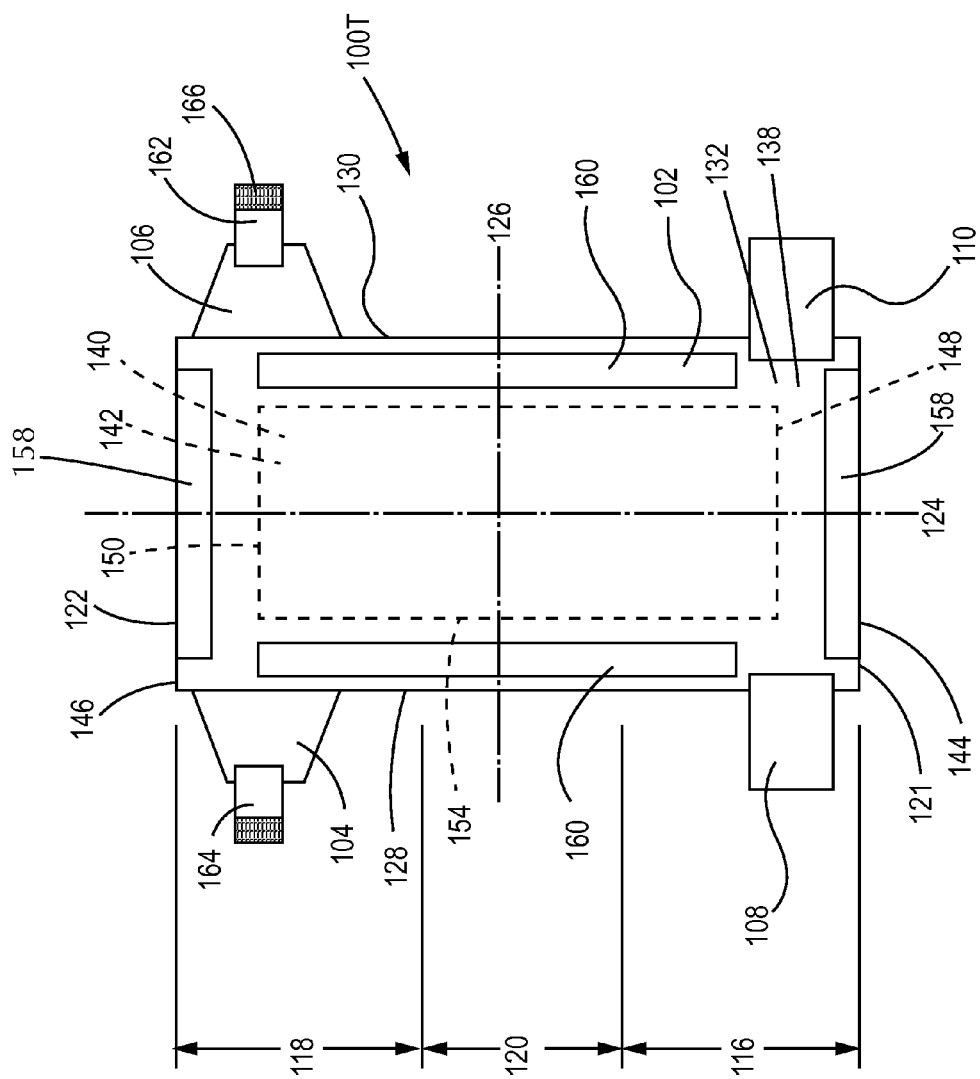
FIG. 1A is plan view of the taped diaper of FIG. 1 with the portion of the diaper that faces away toward a wearer oriented towards the viewer.
Figure 2:
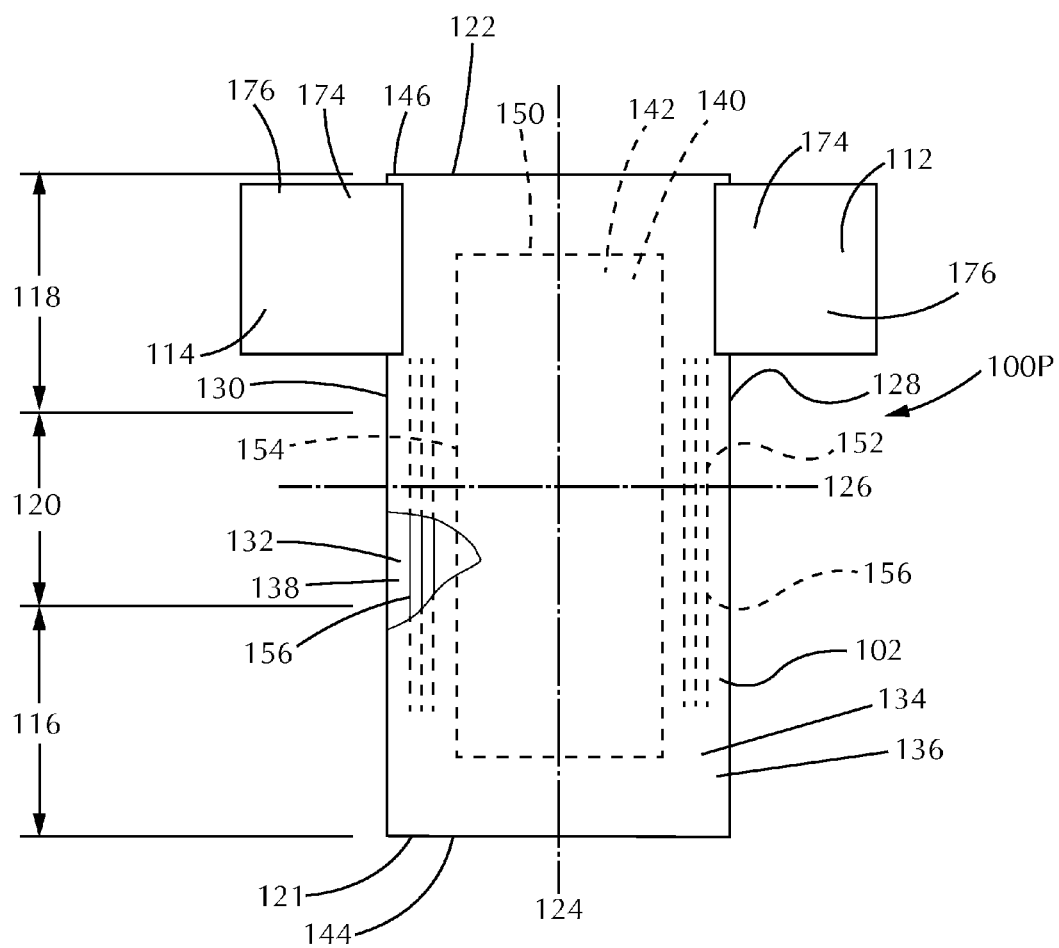
FIG. 2 is a partially cut away plan view of a pant diaper with a pair of side panels.
Figure 3:
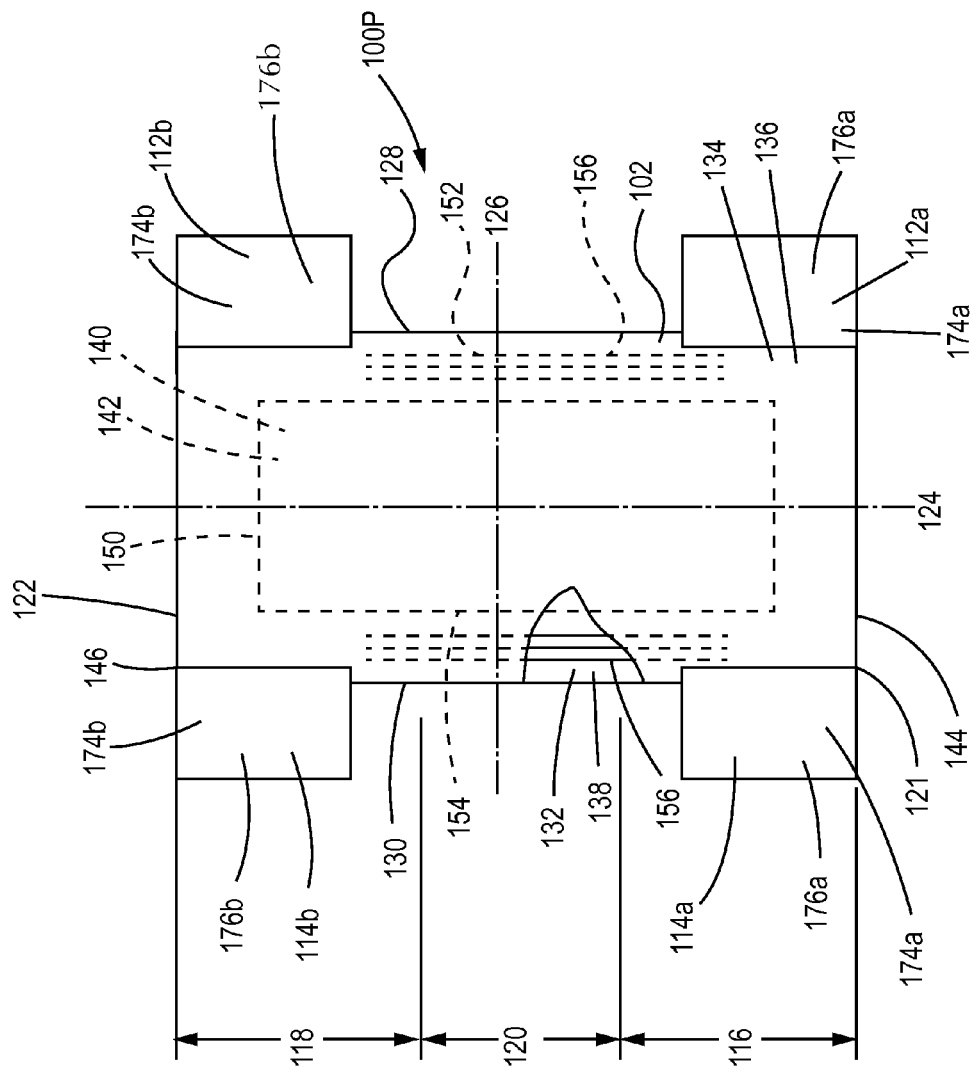
FIG. 3 is a partially cut away plan view a pant diaper with front and rear side ear panels.

The following provides a general description of various types of taped diapers and pant diapers that may be produced with the methods and apparatuses disclosed herein to help provide additional context to the subsequent discussion of the reconfigurable converting lines. For example, FIG. 1 shows one example of a plan view of a taped diaper 100T, with the portion of the diaper that faces away from a wearer oriented towards the viewer. And FIG. 1A shows a plan view of the taped diaper 100T with the portion of the diaper that faces toward a wearer oriented towards the viewer. The taped diaper 100T shown in FIGS. 1 and 1A includes a chassis 102, first and second back ears 104 and 106; and first and second front ears 108 and 110. FIG. 2 shows a diaper pant 100P in a flat, unfolded condition, with the portion of the diaper that faces away from a wearer oriented towards the viewer. The pant diaper 100P shown in FIG. 2 also includes a chassis 102 and opposing first and second side panels 112 and 114 (the first and second side panels may also be referred to as first and second back ears). FIG. 3 shows a diaper pant 100P and chassis 102 in a flat, unfolded condition, with the portion of the diaper that faces away from a wearer oriented towards the viewer. However, the diaper pant 100P of FIG. 3 includes first and second rear ear panels 112b and 114b, and first and second front ear panels 112a and 114a.

Although pant and taped diapers may have distinct different features and components, it is to be appreciated that taped and pant diapers may include many features and components that are substantially the same or similar with regard to disposition, structure, dimension, physical appearance, etc. For the purposes of a specific illustration, various common components of taped and pant diapers shown in FIGS. 1-6 are described below before discussing different features and/or components between the taped and pant diapers.

As shown in FIGS. 1-3, the diapers 100T and 100P are shown as having a first waist region 116, a second waist region 118, and a crotch region 120 disposed intermediate the first and second waist regions. The first waist region 116 may be configured as a front waist region, and the second waist region 118 may be configured as back waist region. In some embodiments, the length of each of the front waist region, back waist region, and crotch region may be ⅓ of the length of the absorbent article 100P and 100T. The absorbent articles 100P and 100T may each include a laterally extending front waist edge 121 in the front waist region 116 and a longitudinally opposing and laterally extending back waist edge 122 in the back waist region 118. To provide a frame of reference for the present discussion, the diapers 100T and 100P in FIGS. 1-3 are shown with a longitudinal axis 124 and a lateral axis 126. The longitudinal axis 124 may extend through a midpoint of the front waist edge 121 and through a midpoint of the back waist edge 122. And the lateral axis 126 may extend through a midpoint of a first longitudinal or right side edge 128 and through a midpoint of a second longitudinal or left side edge 130.

As shown in FIGS. 1-3, the diapers 100T and 100P each include an inner, body facing surface 132, and an outer, garment facing surface 134. The chassis 102 may include a backsheet 136 and a topsheet 138. An absorbent assembly 140 including an absorbent core 142 may be disposed between a portion of the topsheet 138 and the backsheet 136. As discussed in more detail below, the diapers 100T and 100P may also include other features, such as leg elastics, an elastic waist region, and/or flaps, e.g. side panels and/or ears, to enhance the fits around the legs and waist of the wearer.

With continued reference to FIGS. 1-3, the periphery of the chassis 102 may be defined by the first longitudinal side edge 128, a second longitudinal side edge 130; a first laterally extending end edge 144 disposed in the first waist region 116; and a second laterally extending end edge 146 disposed in the second waist region 118. Both side edges 128 and 130 extend longitudinally between the front waist edge 121 and the back waist edge 122. The laterally extending end edges 144 and 146 of the chassis may form a portion of the laterally extending front waist edge 121 in the front waist region 116 and a portion of the longitudinally opposing and laterally extending back waist edge 122 in the back waist region 118. When either the taped diaper 100T or the pant diaper 100P is worn on the lower torso of a wearer, the front waist edge 121 and the back waist edge 122 of the chassis 102 may encircle a portion of the waist of the wearer. At the same time, the chassis side edges 128 and 130 may encircle at least a portion of the legs of the wearer. And the crotch region 120 may be generally positioned between the legs of the wearer with the absorbent core 142 extending from the front waist region 116 through the crotch region 120 to the back waist region 118.

It is to also be appreciated that a portion or the whole of the diapers 100T and 100P may also be made laterally extensible. The additional extensibility may help allow the diapers 100T and 100P to conform to the body of a wearer during movement by the wearer. The additional extensibility may also help, for example, allow the user of the diaper 100T and 100P including a chassis 102 having a particular size before extension to extend the front waist region 116, the back waist region 118, or both waist regions of the diaper 100T and 100P and/or chassis 102 to provide additional body coverage for wearers of differing size, i.e. to tailor the diaper to an individual wearer. Such extension of the waist region or regions may give the absorbent article a generally hourglass shape, so long as the crotch region is extended to a relatively lesser degree than the waist region or regions, and may impart a tailored appearance to the article when it is worn.

As previously mentioned, the taped and pant diapers 100T and 100P may include a backsheet 136. The backsheet 136 may also define the outer surface 134 of the chassis 102. The backsheet 136 may be impervious to fluids (e.g., menses, urine, and/or runny feces) and may be manufactured from a thin plastic film, although other flexible liquid impervious materials may also be used. The backsheet 136 may prevent the exudates absorbed and contained in the absorbent core from wetting articles which contact the diaper 100T and 100P, such as bedsheets, pajamas and undergarments. The backsheet 136 may also comprise a woven or nonwoven material, polymeric films such as thermoplastic films of polyethylene or polypropylene, and/or a multi-layer or composite materials comprising a film and a nonwoven material (e.g., having an inner film layer and an outer nonwoven layer). The backsheet may also comprise an elastomeric film. An example backsheet 140 may be a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet 136 may also be embossed and/or matte-finished to provide a more clothlike appearance. Further, the backsheet 136 may permit vapors to escape from the absorbent core (i.e. the backsheet is breathable) while still preventing exudates from passing through the backsheet 136. The size of the backsheet 136 may be dictated by the size of the absorbent core 142 and/or particular configuration or size of the diaper 100T and 100P.

Also described above, the taped and pant diapers 100T and 100P may include a topsheet 138. The topsheet 138 may also define all or part of the inner surface 132 of the chassis 102. The topsheet 138 may be compliant, soft feeling, and non-irritating to the wearer's skin. It may be elastically stretchable in one or two directions. Further, the topsheet 138 may be liquid pervious, permitting liquids (e.g., menses, urine, and/or runny feces) to penetrate through its thickness. A suitable topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Suitable woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art.

Topsheets 138 may be selected from high loft nonwoven topsheets, apertured film topsheets and apertured nonwoven topsheets. Apertured film topsheets may be pervious to bodily exudates, yet non-absorbent, and have a reduced tendency to allow fluids to pass back through and rewet the wearer's skin. Example apertured films may include those described in U.S. Pat. Nos. 5,628,097; 5,916,661; 6,545, 197; and 6,107,539.

As mentioned above, the taped and pant diapers 100P and 100T may also include an absorbent assembly 140 that is joined to the chassis 102. As shown in FIGS. 1-3, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper 100T, and 100P. Exemplary absorbent structures for use as the absorbent core of the present disclosure are described in U.S. Pat. Nos. 4,610,678; 4,673,402; 4,888,231; and 4,834,735.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprises primarily absorbent gelling material (AGM) in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 and 2004/0097895.

As previously mentioned, the taped diapers 100T and pant diapers 100P may also include elasticized leg cuffs 156 and an elasticized waistband 158. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695, 278; 4,795,454; 4,704,115; 4,909,803; and U.S. Patent Publication No. 2009/0312730A1.

The elasticized waistband 158 may provide improved fit and containment and may be that portion or zone of the diaper 100T and 100P that may elastically expand and contract to dynamically fit a wearer's waist. The elasticized waistband 158 may extend longitudinally inwardly from the waist edges 120, 122 of the diaper toward the lateral edges 148, 150 of the absorbent core 142. The diaper 100T and 100P may also include two elasticized waistbands 158, one positioned in the back waist region 118 and one positioned in the front wait region 116, although other embodiments may be constructed with a single elasticized waistband 158. The elasticized waistband 158 may be constructed in a number of different configurations including those described in U.S. Pat. Nos. 4,515,595 and 5,151,092.

The elasticized waistbands 158 may include materials that have been "prestrained" or "mechanically prestrained" (i.e. subjected to some degree of localized pattern mechanical stretching to permanently elongate the material). The materials may be prestrained using deep embossing techniques as are known in the art. In some embodiments, the materials may be prestrained by directing the material through an incremental mechanical stretching system as described in U.S. Pat. No. 5,330,458. The materials are then allowed to return to their substantially untensioned condition, thus forming a zero strain stretch material that is extensible, at least up to the point of initial stretching. Examples of zero strain materials are disclosed in U.S. Pat. Nos. 2,075,189; 3,025,199; 4,107,364; 4,209,563; 4,834,741; and 5,151,092.

As shown in FIGS. 1-3, the chassis 102 may have longitudinally extending and laterally opposing side flaps 160 that are disposed on the interior surface 132 of the chassis 102 that faces inwardly toward the wearer and contacts the wearer. Each side flap may have a proximal edge. The side flaps may also overlap the absorbent assembly 140, i.e. the proximal edges extend laterally inward of the respective side edges of the absorbent assembly 152 and 154. In some configurations, the side flaps may not overlap the absorbent assembly. It is to be appreciated that the side flaps may be formed in various ways, such as for example, by folding portions of the chassis 102 laterally inward, i.e. toward the longitudinal axis 124, to form both the respective side flaps and the side edges 128 and 130 of the chassis 102. In another example, the side flaps may be formed by attaching an additional layer or layers to the chassis at or adjacent to each of the respective side edges and of the chassis. Each of the side flaps may be joined to the interior surface 132 of the chassis and/or the absorbent assembly in side flap attachment zones in the front waist region 116 and in side flap attachment zones in the back waist region 118. The side flaps may extend to the same longitudinal extent as the absorbent article or alternatively the side flaps may have a longitudinal extent that is less than the absorbent article.

As previously mentioned, pant and taped diapers may have distinct different features and/or components. And the following provides a general discussion of some such features and components with reference to accompanying figures showing embodiments of taped and pant diapers.

Figure 4:
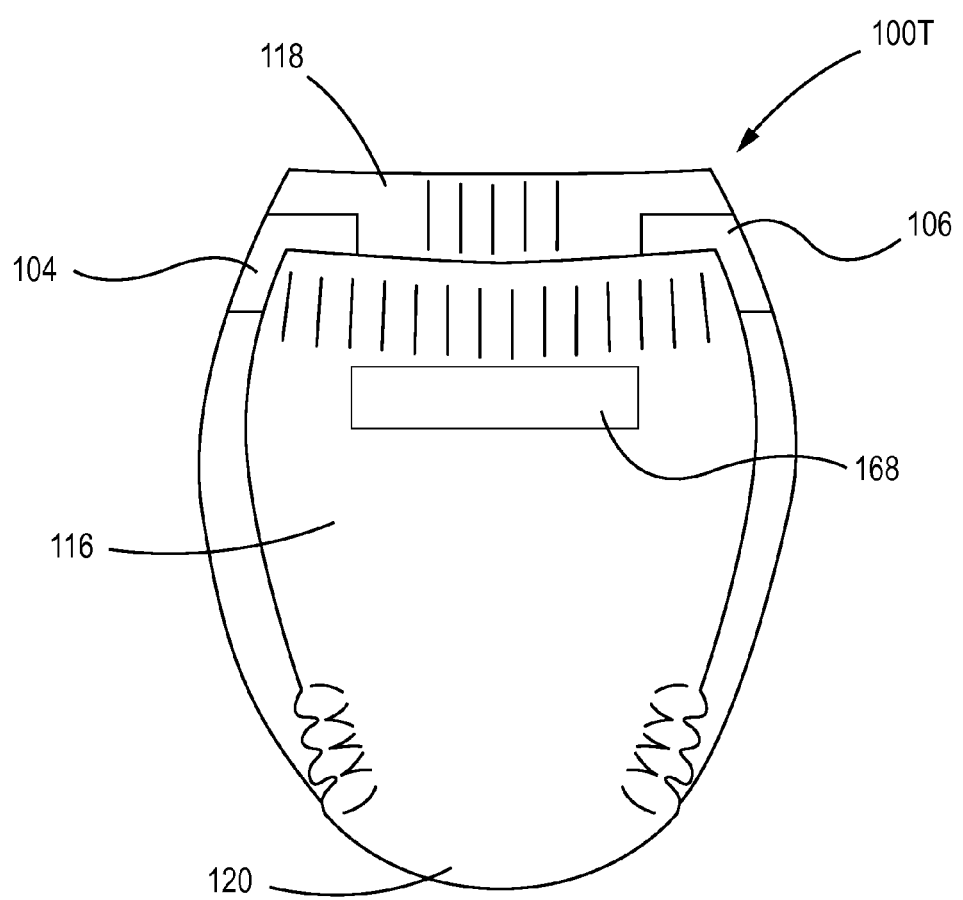
FIG. 4 is a perspective of the taped diaper shown in FIG. 1 in a folded configuration.

Taped diapers may be manufactured and provided to consumers in a configuration wherein the front waist region and the back waist region are not fastened, pre-fastened, or connected to each other as packaged, prior to being applied to the wearer. As shown in FIG. 4, for example, the taped diaper 100T may be folded about a lateral centerline with the interior surface 132 of the first waist region 116 in surface to surface contact with the interior surface 132 of the second waist region 118 without fastening or joining the waist regions together. The back ears 104 and 106 and/or the front ears 108 and 110 when present may also be folded laterally inward toward the inner surfaces 132 of the waist regions 116 and 118.

The taped diaper 100T may include various configurations of fastening elements to enable fastening of the front waist region 116 and the back waist region 118 together to form a closed waist circumference and leg openings once the diaper is positioned on a wearer. For example, as shown in FIG. 1A, the taped diaper 100T may include first and second back ears 104 and 106 and first and second front ears 108 and 110, wherein the first and second back ears 104 and 106 are configured to include fastening components 162 and 164. Each fastening component 162 and 164 may form a portion of or may be permanently bonded, adhered or otherwise joined directly or indirectly to the chassis 102 laterally inward from the side edge 128 and 130, in one of the front waist region 116 or the back waist region 118. Alternatively, the fastening component 162 and 164 may form a portion of or may be permanently bonded, adhered or otherwise joined directly or indirectly to the first and second back ears 104 and 106 at or adjacent the distal edge of the ear and/or the first and second front ears 108 and 110 at or adjacent the distal edge of the ear. The fastening components may also be permanently bonded or joined at or adjacent the side edges 128 and 130 of the absorbent article in various ways, such as for example, by adhesive bonds, sonic bonds, pressure bonds, thermal bonds or combinations thereof.

The first fastening component 162 and/or the second fastening component 164 may include various types of releasably engageable fasteners. The first and second fastening components 162 and/or 164 may also include various types of refastenable fastening structures. For example, the first and second fastening components 162 and 164 may include mechanical fasteners, 166, in the form of hook and loop fasteners, hook and hook fasteners, macrofasteners, buttons, snaps, tab and slot fasteners, tape fasteners, adhesive fasteners, cohesive fasteners, magnetic fasteners, hermaphrodidic fasteners, and the like. Some examples of fastening systems and/or fastening components 162, 164 are discussed in U.S. Pat. Nos. 3,848,594; 4,662,875; 4,846,815; 4,894,060; 4,946,527; 5,151,092; 5,221,274; 6,251,097; 6,669,618; 6,432,098; and U.S. Patent Publication Nos. 2007/0078427 and 2007/0093769.

As previously mentioned, the fastening components 162 and 164 may be adapted to releasably and/or refastenably engage or connect with another portion of the diaper 100T. For example, as shown in FIG. 1, the diaper 100T may include a connection zone 168, sometimes referred to as a landing zone, in the first waist region 116. As such, when the taped diaper 100T is placed on a wearer, the fasteners 162 and 164 are pulled around the waist of the wearer and connected with the connection zone 168 in the first waist region 116 to form a closed waist circumference and a pair of laterally opposing leg openings. It is to be appreciated that the connection zone may be constructed from a separate substrate that is connected with the chassis 102 of the taped diaper. In some embodiments, the connection zone may be integrally formed as part of the backsheet 136 of the diaper 100T or may be formed as part of the first and second ears in one or both of the waist regions, such as described in U.S. Pat. Nos. 5,735,840 and 5,928,212.

The taped diaper 100T may further include a non-engagement zone disposed on the same surface and in the same waist region as the fastening components 166. The non-engagement zone may be configured to help prevent the fastening component 166 from becoming engaged with other elements of the absorbent article. The non-engagement zone may comprise a film, coating or other material that does not attach to or engage with the fastening component 166. In certain embodiments the non-engagement zone is in surface to surface contact with the fastening surface of the fastening component when the taped diaper 100T is packaged.

In contrast to taped diapers, pant diapers may be manufactured and provided to consumers in a configuration wherein the front waist region and the back waist region are fastened, pre-fastened, or connected to each other as packaged, prior to being applied to the wearer. As such pant diapers may have a continuous perimeter waist opening and continuous perimeter leg openings designed for infant or adult wearers. As discussed in more detail below, a diaper pant can be preformed by various techniques including, but not limited to, joining together portions of the diaper using refastenable and/or permanent closure members (e.g., seams, heat bonds, pressure welds, adhesives, cohesive bonds, mechanical fasteners, etc.). In addition, pant diapers can be preformed anywhere along the circumference of the waist region (e.g., side fastened or connected, front waist fastened or connected, rear waist fastened or connected).

Figure 5:
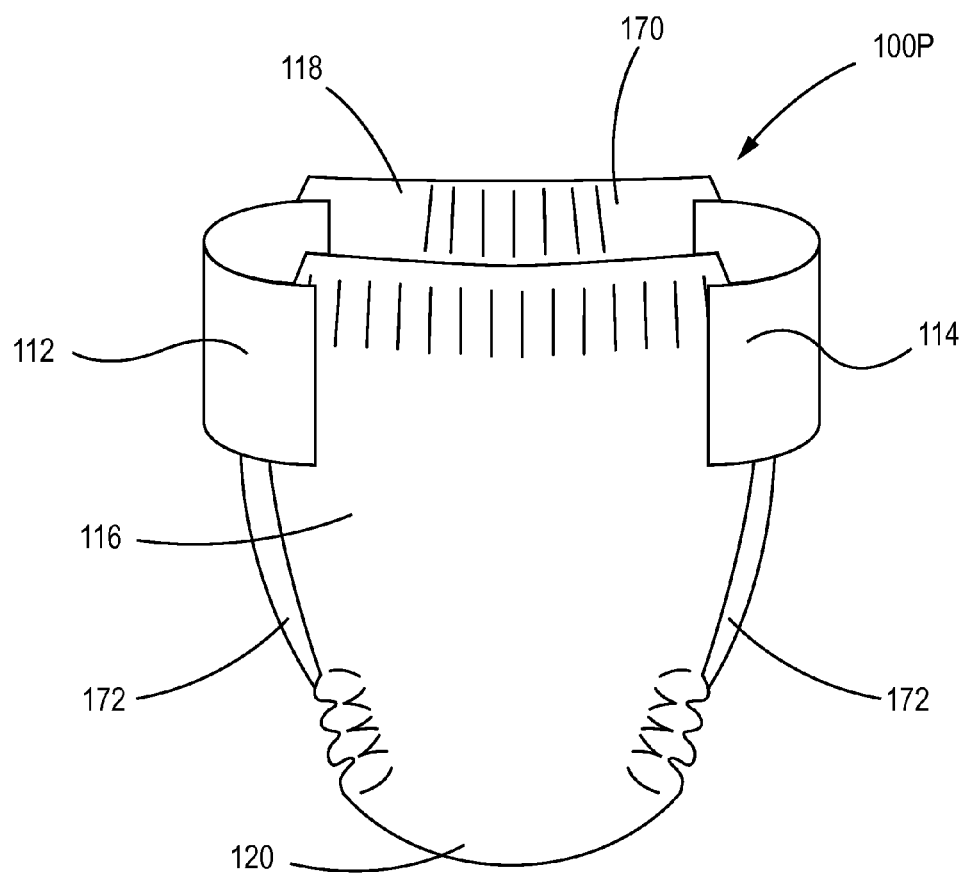
FIG. 5 is a perspective view the pant diaper shown in FIG. 2 with side panels connecting opposing waist regions.

In some embodiments, pant diapers may be configured with side panels connected with the chassis in one or both of the waist regions. For example, FIGS. 2 and 5 show a pant diaper 100P including first and second side panels 112 and 114 connected with the rear waist region 118. The side panels 112 and 114 may be attached at or adjacent the side edges 128 and 130 of the chassis 102. The side panels 112 and 114 may be substantially rectangular in shape or the side panels may be shaped in such a way as to provide an integral tab for ease of opening and refastening. The side panels may be also be extensible in at least the lateral direction. The side panels may also be elastically extensible in the lateral direction. Furthermore, the side panels may be elastically extensible in both the longitudinal and lateral directions. The side panels may comprise a film, a nonwoven or a combination of film and nonwoven. The side panels may also comprise a plurality of strand-like filaments and a nonwoven. The strand-like elements may also be elastically extensible in at least the lateral direction.

As previously mentioned and with reference to FIGS. 2 and 5, the first and second side panels 112 and 114 may connect the first waist region 116 with the second waist region 118 of the chassis 102 to form a waist opening 170 and two leg openings 172. For example, proximal end regions 174 of the first and second side panels 112 and 114 are connected with the rear waist region 118 of the chassis 102 and distal end regions 176 of the first and second side panels 112 and 114 are connected with the front waist region 116 of the chassis to the form the pant diaper 100P.

It is to be appreciated that the either or both the distal and proximal regions of one or both the side panels 114 and 116 may be connected with the chassis in various ways. For example, in some configurations, the side panels are permanently connected with opposing waist regions and cannot be refastened once broken forming the leg and waist openings. Such permanent seams are pre-closed to provide a product that looks like underwear and can be applied like underwear, i.e. pulled-on. Disposable pant diapers with permanent seams may require a separate element for disposal such as a disposal tape disposed on the outer surface of the article. Other disposable pant diapers may have non-permanent seams and may be refastenable allowing the caregiver to open the initial waist opening circumference and leg openings and reclose them to facilitate application similar to a traditional tape style diaper. As such, the proximal regions and/or distal regions of the side panels may be permanently bonded, releasably connected, and/or refastenably connected with the chassis 102, with for example, adhesives, cohesives, thermal bonding, ultrasonic bonding, mechanical bonding and mechanical fastening e.g. hook and loop type fasteners. For example, one or more fastener elements may be located on or form a portion of the side panels and may be adapted to refastenably connect with one or more corresponding fastening elements located in the first or second waist regions or alternatively the fastener elements may be adapted to refastenably connect with one or more components of the absorbent article including the side panels. The diaper pant 100P can also include other features such as elastically extensible side panels that may each include one or more pieces of material. It should be appreciated that the side panels may also be formed as continuous extensions of the first and second waist regions of the chassis.

The ability to refasten an initially pre-fastened pant diaper may offer convenience to the caregiver. In some instances, it may be more convenient to apply the absorbent article like a traditional tape style diaper when away from home or when it is inconvenient to remove the clothing and/or shoes. Because it is difficult to predict when a change will be necessary and therefore when a particular mode of application will be needed, it is beneficial to have a disposable pant diaper that is adaptable to being applied either as a traditional tape style diaper or as a disposable pant diaper, pull-on. In addition, an absorbent article that can be applied like a traditional tape style diaper or a disposable pant diaper also permits inspection of the interior of the product without having to pull the product down. These refastenable structures may also provide dual functionality enabling the wrapping and disposal of the used product.

Figure 6:
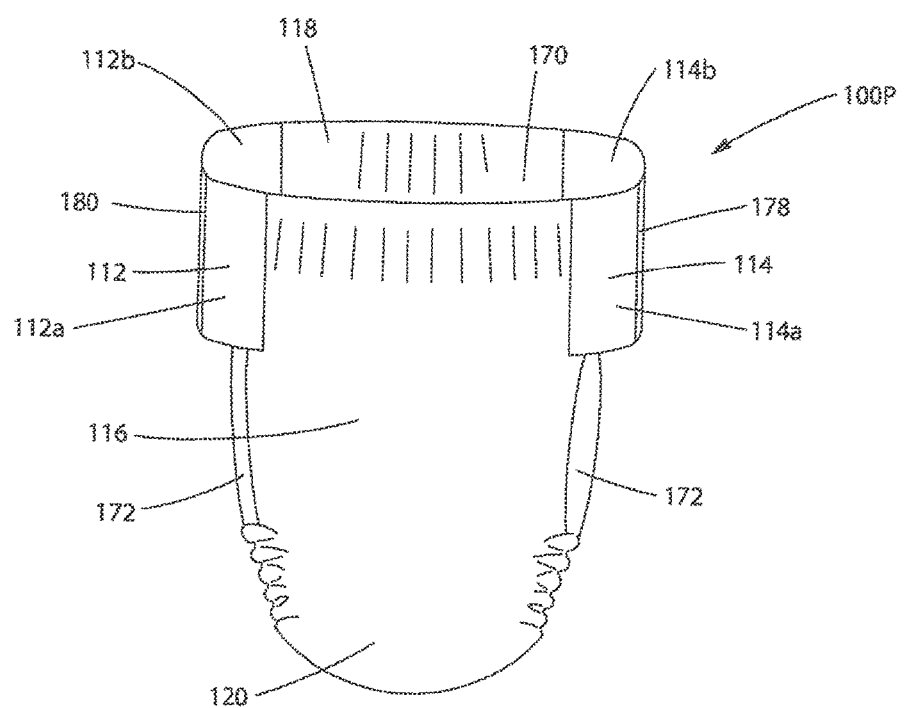
FIG. 6 is a perspective view the pant diaper shown in FIG. 3 with side seams connecting the ear panels and opposing waist regions.

As previously mentioned, the side panels on pant diapers can be configured in different ways. Although the side panels 112 and 114 shown in FIGS. 2 and 5 may be of a single unitary piece construction, it is to be appreciated that the side panels may be formed by connecting ear panels together. In some embodiments, pant diapers may be configured with side panels connected with the chassis in both of the waist regions. For example, FIGS. 3 and 6 show a pant diaper 100P wherein the first side panel 112 includes a first ear panel 112a connected with a second ear panel 112b, and the second side panel 114 includes a first ear panel 114a connected with a second ear panel 114b. The first ear panels 112a, 114a each include proximal regions 174a connected with the first waist region 116 of the chassis 102. And second ear panels 112b, 114b each include proximal regions 174b connected with the second waist region 118 of the chassis 102. A distal region 176a of the first ear panel 112a and a distal region 176b of the second ear panel 112b may be connected with each other along a first side seam 178 to form the first side panel 112. And a distal region 176a of the first ear panel 114a and a distal region 176b of the second ear panel 114b may be connected with each other along a second side seam 180 to form the second side panel 114.

It is to be appreciated that the proximal regions of the ear panels of FIGS. 3 and 6 may be connected with the chassis in various ways, and the distal regions of the ear panels may be connected with each other in various ways. For example, the proximal regions and/or distal regions of the side panels may be permanently bonded, releasably connected, and/or refastenably connected with the chassis and/or each other, with for example, adhesives, cohesives, thermal bonding, ultrasonic bonding, mechanical bonding and mechanical fastening e.g. hook and loop type fasteners. For example, one or more fastener elements may be located on the side panels and may be adapted to refastenably connect with one or more corresponding fastening elements located in the first or second waist regions or alternatively the fastener elements may be adapted to refastenably connect with one or more components of the absorbent article including the side panels. The diaper pants can also include other features such as elastically extensible side panels that may each include one or more pieces of material.

It should also be appreciated that the side panels in one waist region may have the same lateral extent from the side edge of the chassis to the distal edge of the side panel as the longitudinally opposed side panels in the opposite waist region or alternatively the side panels disposed in a first waist region may have different lateral extent as measured from the side edge of the chassis to the distal edge of the side panel than the side panels disposed in a second waist region.

As such, for a pant diaper including side seams, a first portion of the pant diaper 100P adjacent the first side edge 128 in the front waist region 116 and a second portion of the pant diaper adjacent the first side edge 128 in the back waist region 118 may be connected to form a first permanent side edge seam 178. And a third portion of the pant diaper 100P adjacent the second side edge 130 in the front waist region 116 and a fourth portion of the pant diaper adjacent the second side edge 130 in the back waist region 118 may be connected to form a second permanent side edge seam 180. The connection of the side edge seams 178 and 180 define the initial waist opening 170 circumference and a pair of leg openings 172. In another configuration, a pant diaper 100P may include a first mating fastening component having a fastening surface and an opposing attachment surface wherein the attachment surface is joined directly to one of the interior or exterior surface of the pant diaper in a first waist region. The pant diaper may further comprise a second mating fastening component having a fastening surface and an opposing attachment surface wherein the attachment surface may be joined directly to the same surface of the pant diaper as the first fastening component. The second mating fastening component may be joined to or may form a portion of the surface to which the attachment surface of the first mating fastening component is joined.

In yet another configuration, the pant diaper may include a frangible separation zone that may be disposed laterally inward of the side edge seams 178 and 180 that allows the initial waist opening circumference 170 and leg openings 172 of the pant 100P to be opened for removal or to enable application as a traditional tape style diaper. As discussed above, the pant diaper may further include a first fastening component and a second fastening component disposed in one of the front or back waist regions 116 and 118. And each of the fastening components may be disposed on the same surface of the pant diaper 100P, e.g., the exterior surface 134. The fastening components may be capable of being fastened in a traditional tape style diaper fashion or fastened to reform a secondary waist opening circumference and leg openings after the initial waist opening circumference and leg openings have been broken. In addition, the fastening components can be used to aid disposal of a soiled pant.

As previously mentioned, the bonds of the side edge seams 178 and 180 may be permanent and can be formed in various ways appropriate for the specific materials employed. Thus, example bond types may include discrete bonds such as sonic sealed bonds, heat sealed bonds, high pressure bonds, radio frequency bonds, adhesive or cohesive bonds, sewed bonds, autogeneous bonds, and combinations thereof. In accordance with one aspect of the disclosure, the permanent side edge seams 178 and 180 may be joined by a predetermined pattern of heat/pressure or ultrasonic welds which withstands the forces and stresses exacted onto the side edge seam 51 during application and wear of the pant 20. The permanent side edge seams 178, 180 may be formed as disclosed in U.S. Pat. Nos. 5,779,831; 5,772,825; 5,607,537; 5,622,589; 5,662,638; 6,042,673; and 6,726,792.

Because the pant diaper 100P may be configured with permanent side edge seams 178 and 180, both permanent side edge seams may be pre-closed, meaning that the side edge seams are closed prior to removal of the diaper pant from its package, and therefore prior to being donned on the wearer. The pre-closed permanent side edge seams 178 and 180 may form an initial waist opening circumference and leg circumferences. The initial waist opening circumference and leg circumferences may be opened at predetermined frangible separation zones. The permanent side edge seams cannot be reclosed to form the secondary waist opening circumference and leg openings.

Additionally, various diaper pant configurations are disclosed in U.S. Pat. Nos. 5,246,433; 5,569,234; 6,120,487; 6,120,489; 4,940,464; 5,092,861; 5,897,545; 5,957,908; and U.S. Patent Publication Nos. 2003/0233082; 2005/0234419; 2003/0088220; 2005/0130821; 2003/0233082; 2005/0215971; 2005/0215970; 2007/0078427; 2007/0093769; 2007/0074381; 2007/0078426; and 2008/0107861.

As previously discussed, converting apparatuses and methods for manufacturing taped and pant diapers according to the present disclosure are adapted to operate in at least a first configuration and a second configuration. And the converting apparatus includes transformation mechanisms adapted to produce a series of transformations. In a first configuration, a first plurality of the transformation mechanisms are arranged to produce a plurality of taped diapers, wherein the first plurality of the transformation mechanisms produce a first number of transformations. In a second configuration, a second plurality of the transformation mechanisms are arranged to produce a plurality of pant diapers, wherein the second plurality of the transformation mechanisms produce a second number of transformations. As discussed in more detail below with reference to FIGS. 8-10, the converting apparatus may be configured with relatively high flexibility in changing between the first and second configurations, because a relatively large percentage of transformations remain the same in both configurations.

Figure 8:
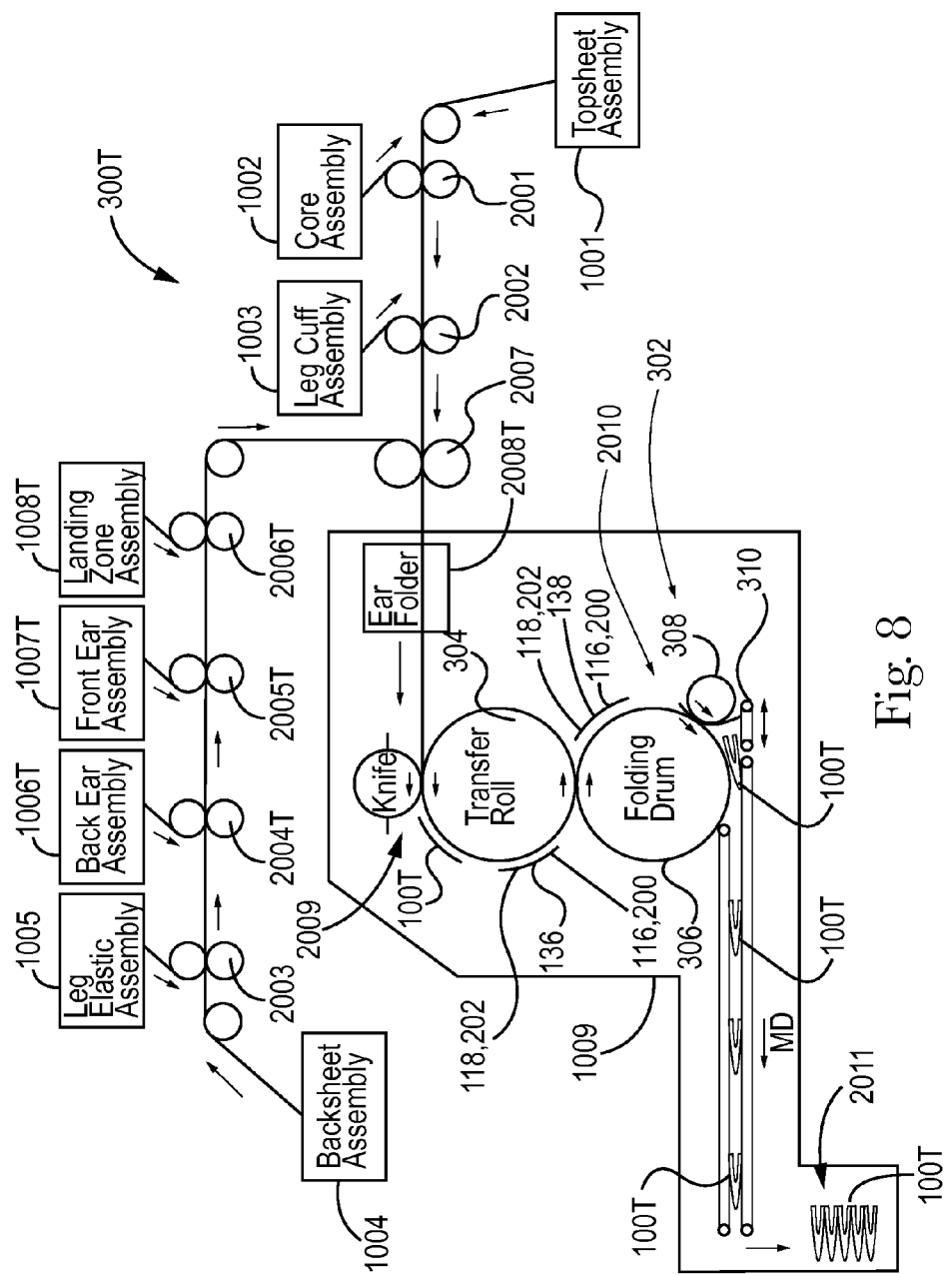
FIG. 8 is a schematic side view of a converting apparatus in a first, taped diaper, configuration adapted to manufacture taped diapers.

FIG. 8 shows a schematic view of a converting apparatus 300 in a first configuration adapted to manufacture taped diapers 100T. The method of operation of the converting apparatus 300 may described with reference to the various components of taped diapers 100T described above and shown in FIGS. 1, 1A, and 4. It is to be appreciated transformations shown and described herein can be carried out in various different orders than that which is depicted and described herein. As shown in FIG. 8, a topsheet assembly process is completed at step 1001, and a core assembly process is completed at step 1002. The core assembly is combined with the advancing topsheet substrate at transformation 2001. In addition, a leg cuff assembly process is completed at step 1003 and is combined with the advancing topsheet at transformation 2002 forming the topsheet substrate. At the same time, a backsheet assembly process may be completed at step 1004, and a leg elastic assembly process is completed at step 1005. The leg elastics are combined with the advancing backsheet substrate at transformation 2003. In addition, a back ear assembly process is completed at step 1006T; a front ear assembly process is completed at step 1007T; and a landing zone assembly process is completed at step 1008T. The back ears, front ears, and landing zone are combined with the advancing backsheet substrate at transformations 2004T, 2005T, and 2006T, respectively forming the backsheet substrate. Next, the advancing backsheet substrate and topsheet substrate are combined at transformation 2007 to create a continuous length of taped diapers. And the continuous length of taped diapers is subjected to a final forming process at step 1009.

Figure 8A:
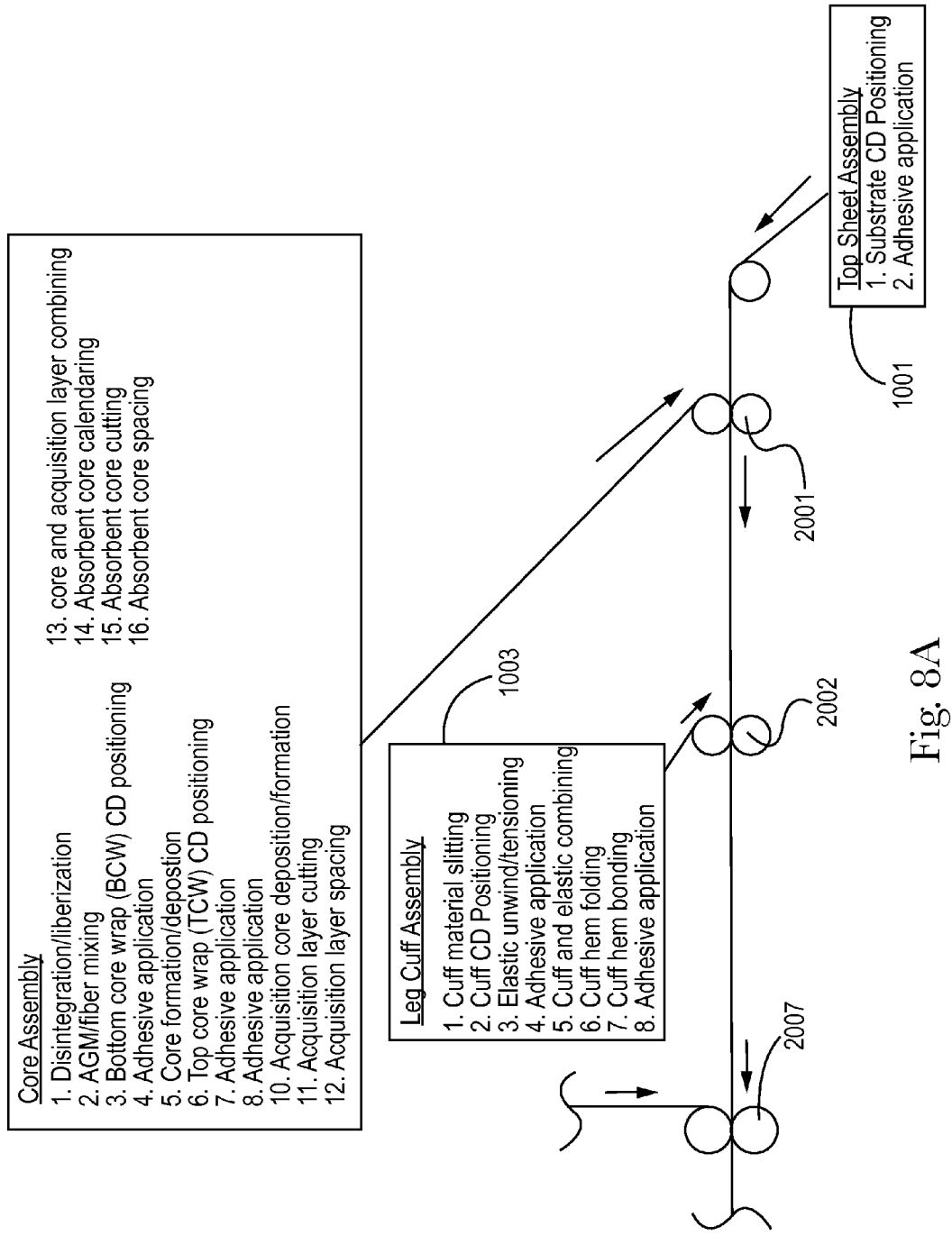
FIG. 8A is a partial detailed view of FIG. 8 showing transformations of particular processes.

It is to be appreciated that one or more transformations may occur during each process step shown in FIG. 8. For example, as shown in FIG. 8A the topsheet assembly process 1001 may include 2 transformations, such as for example: (1) Substrate CD positioning; and (2) Adhesive application. The core forming process 1002 may include 16 transformations, such as for example: (1) Disintegration/fiberization; (2) AGM/fiber mixing; (3) Bottom core wrap (BCW) CD positioning; (4) Adhesive application; (5) Core formation/deposition; (6) Top core wrap (TCW) CD positioning; (7) Adhesive application; (8) BCW, core and TCW combining; (9) Adhesive application; (10) Acquisition core deposition/formation; (11) Acquisition layer cutting; (12) Acquisition layer spacing; (13) Core and acquisition layer combining; (14) Absorbent core calendaring; (15) Absorbent core cutting; and (16) Absorbent core spacing. And the leg cuff assembly process 1003 may include 8 transformations, such as for example: (1) Cuff material slitting; (2) Cuff CD Positioning; (3) Elastic unwind/tensioning; (4) Adhesive application; (5) Cuff and elastic combining; (6) Cuff hem folding; (7) Cuff hem bonding; and (8) Adhesive application.

Figure 8B:
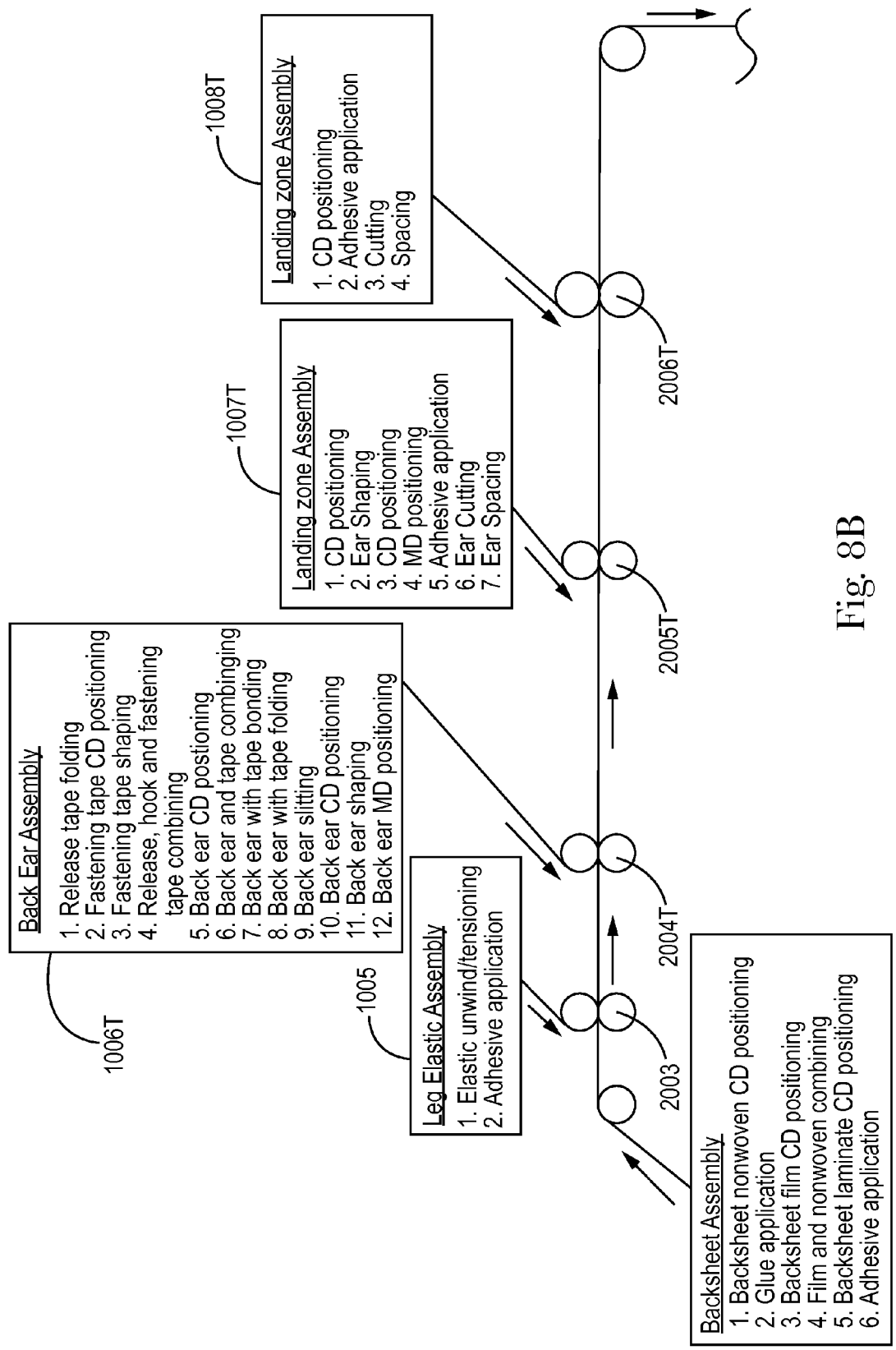
FIG. 8B is a partial detailed view of FIG. 8 showing transformations of particular processes.

In other examples, such as shown in FIG. 8B, the backsheet assembly process 1004 may include 6 transformations, such as for example: (1) Backsheet nonwoven CD positioning; (2) Glue application; (3) Backsheet film CD positioning; (4) Film and nonwoven combining; (5) Backsheet laminate CD positioning; and (6) Adhesive application. The leg elastic assembly 1005 may include 2 transformations, such as for example: (1) Elastic unwind/tensioning; and (2) Adhesive application. The back ear assembly 1006T may include 12 transformations, such as for example: (1) Release tape folding; (2) Fastening tape CD positioning; (3) Fastening tape shaping; (4) Release, hook and fastening tape combining; (5) Back ear CD positioning; (6) Back ear and tape combining; (7) Back ear with tape bonding; (8) Back ear with tape folding; (9) Back ear slitting; (10) Back ear CD positioning; (11) Back ear shaping; and (12) Back ear MD positioning. The front ear assembly 1007T may include 7 transformations, such as for example: (1) CD positioning; (2) Ear Shaping; (3) CD positioning; (4) MD positioning; (5) Adhesive application; (6) Ear Cutting; and (7) Ear Spacing. And the landing zone assembly 1008T may include 4 transformations, such as for example: (1) CD positioning; (2) Adhesive application; (3) Cutting; and (4) Spacing.

Referring back to FIG. 8, the final forming process 1009 may include 4 transformations. For example, the final forming process 1009 for taped diapers may include a front and back ear folding transformation 2008T. In the front and/or back ear folding transformation 2008T, the continuous length of taped diapers may be subjected to a process wherein folding bars or other type of mechanism folds the front ears 108 and 110 and/or back ears 104 and 106 laterally inward toward each other and onto the inner surfaces 132 of the taped diapers 100T, such as shown in FIG. 4. The final forming process 1009 may also include a final knife cut transformation 2009 wherein the continuous length of taped diapers are cut into separate and discrete taped diapers 100T. The discrete diapers may also be subjected to a folding transformation 2010 wherein each diaper is folded along a laterally extending fold line, such as shown in FIG. 4. Finally, the taped diapers may be subjected to stacking transformation 2011 wherein folded taped diapers are stacked and prepared for packing.

As previously mentioned, the core assembly process 1002 may include a number of different transformations. It is to be appreciated that these transformations may be dependent on the actual composition of the absorbent materials forming the absorbent core. For example, heterogeneous absorbent cores comprising a blend a fibrous material and a particulate material may be formed by a blending transformation that blends, mixes or combines the fibrous component and a particulate component to form a heterogeneous absorbent structure. Examples of such heterogeneous structures may include blends of cellulosic fibers and absorbent gelling material wherein the cellulosic material may be present in a percentage from about 5% to about 95% and the absorbent gelling material present a percentage from about 95% to about 5% respectively. In some embodiments, the heterogeneous structure may comprise a blend of adhesive fibers and absorbent gelling material wherein the adhesive fibers are present in a percentage from about 2% to about 70% and the absorbent gelling material is present in a percentage from about 98% to about 30% respectively. In such embodiments, the cellulosic fibrous material may be supplied to the production line in bale form and/or in drylap form. Both of these forms may require a fiberization step to separate the fibers into individual fibers or small groupings of fibers to facilitate blending/mixing of the fibers with other materials. The absorbent gelling material may be supplied to the production line in particulate form and no further manipulation is required prior to formation of the heterogeneous structure. The individual fibers or small groupings of fibers may be mixed with the absorbent gelling material to form a heterogeneous mixture. The mixture may also be deposited onto a vacuum conveyance such as a vacuum belt or a vacuum drum to form either a continuous web of absorbent material or alternatively a plurality of discrete absorbent cores. The formation of the heterogeneous fiber AGM absorbent core material therefore may include at least three distinct transformations as detailed herein above; fiberization, mixing and deposition.

It is to be appreciated that formation of an absorbent core from a material that is supplied to the production line in roll form is also possible. Examples of such web form absorbent materials include tissue laminates (laminates of tissue and absorbent gelling material), nonwoven laminates (laminates of nonwoven and absorbent gelling material), absorbent foams, high basis weight absorbent tissues, absorbent wadding, thermally bonded cellulosic fiber and absorbent gelling material composites, chemically bonded cellulosic fiber and absorbent gelling material composites and the like. The material may simply be unwound and subsequently severed in the cross machine direction at the desired machine direction length. The material may also be severed in the machine direction, either linearly or in a shaped pattern such as a repeating nested pattern. The cross machine direction cutting and/or the machine direction cutting and/or shaping may also form specific transformation steps as described herein.

The following provides additional explanation of "unwinding," which may be a part of various process assemblies used in the converting line 300 shown in FIGS. 8A and 8B but is not considered to be a transformation. Many materials are supplied to the production line in the form of a continuous web disposed in roll form. Examples of such web materials include films, including polymeric films, elastomeric films, microporous films, monolithic films and the like as well as woven and nonwoven materials, including carded, meltblown and spunbond materials comprising polymeric fibers such as polyethylene, polypropylene and the like as well as fiber materials such as rayon. The materials may be delivered to the production line by means of a material unwind. The material unwind may comprise a splicing unit which splices the end of one roll comprising a continuous web material to the beginning of a subsequent roll of continuous web material. This process may be repeated such that the process may run uninterrupted. The splicing feature may form a transformation, i.e. splicing (e.g. bonding). If the splicing step includes a cutting step, the cutting step may form a separate transformation.

With further regard to unwinding, some materials may be supplied to the production line in the form of composite web, i.e. a web comprising two or more distinct layers or structures, disposed in roll form. Examples of such web materials include composites of films and nonwovens, including polymeric films, elastomeric films, microporous films, monolithic films and the like combined with woven and/or nonwoven materials, such as carded and/or spunbond materials comprising polymeric fibers such as polyethylene, polypropylene and the like. This type of unwind may also comprise a splicing feature. The material splicing feature forms transformations, i.e. splicing (e.g. bonding). If the splicing step includes a cutting step, the cutting step may form a separate transformation.

In addition, materials such as elastics may be supplied to a production line in the form of a film or a continuous strand disposed on a roll or spool. Examples of such strand materials include: lycra elastics, natural rubber elastics, threads, strings and the like. The materials may be delivered to the production line by means of a material unwind. The material unwind may comprise guides to properly space the strands and provide proper orientation of the strand relative to the absorbent article. The unwind may also comprise a tensioning device, metering control, which adds tension to the film or strand which in the case of an elastic extends the elastic thereby controlling the elastic contraction force once applied to the article. In some instances, the production line is stopped to splice in new rolls of strand materials. These materials, in particular, strand materials may have an extremely long run time and therefore the stoppage required for changeover may have a minimal impact on the efficiency of the converting process. A material unwind comprising a tensioning device may form a transformation.

The following provides additional explanation of the transformations referred to as "spacing," which may be a part of various process assemblies used in the converting line 300 shown in FIGS. 8A and 8B. Taped and pant diapers may include multiple components which may have different longitudinal, machine direction, extents as well as different lateral, cross machine direction, extents. For materials that have different machine direction extents certain elements may be spaced apart such that these elements are properly disposed relative to and correspond with other elements of the absorbent article. There are various processes by which these spaces may be created. One such process comprises a first conveyance, such as a vacuum conveyor, having a surface speed and a second conveyance, such as a vacuum conveyor, having a surface speed the surface speed of the second conveyance being greater than the surface speed of the first conveyance whereby transferring a discrete element from the first conveyance to the second conveyance increases the distance between the discrete elements. In such an embodiment the first and second conveyances may form a transformation since both are required to space the element. In another embodiment, the process may include a continuous web wherein the web has a surface speed and a first conveyance, such as a vacuum drum, having a surface speed the surface speed of the first conveyance being greater than the surface speed of the web wherein the web is severed in a cross machine direction transferring a discrete element from the web onto the first conveyance whereby the discrete element is subsequently transported at the higher speed to space the discrete elements appropriately relative to the remainder of the absorbent article. In such a configuration the first conveyance may form a transformation. Additionally severing the web in the cross machine direction may form a separate transformation as described herein.

The following provides additional explanation of the transformations referred to as "adhesive application," and "bonding," which may be a part of various process assemblies used in the converting line 300 shown in FIGS. 8A and 8B. Adhesive bonding may be employed to create a bond within a specific element for example bonding two layers of a folded element together or alternatively to attach two separate elements of an absorbent article together. There are several types of adhesives that can be used to form the bonds including hotmelt adhesives, cohesives, A-B adhesives and the like. An adhesive bond may be disposed in a pattern that may be substantially continuous in one or both of the lateral or longitudinal directions across the absorbent article or it may form an intermittent pattern in one or both of those directions. The adhesive bond may also be in the form of one or more beads, one or more spirals, one or more repeating, e.g. zigzag, or random, e.g. spray, patterns, one or more slot coatings or may be formed by printing of the adhesive. Non-limiting examples of adhesive bonds that may be used in absorbent articles include: backsheet film to backsheet nonwoven bond, backsheet to absorbent assembly bond, absorbent core to core cover bond, storage core to acquisition core bond, absorbent assembly to topsheet bond, backsheet to topsheet bond, backsheet to barrier leg cuff bond, barrier leg cuff to topsheet bond, barrier leg elastic attachment bond, outer leg elastic attachment bond, side panel film to side panel nonwoven bond, waistband to absorbent article bond, side panel to chassis bond, landing zone to backsheet bond, and fastening component to absorbent article bond. Each of these examples may represent a separate transformation within the production line. Generally speaking the process to apply an adhesive bond comprises a reservoir to maintain a supply of the adhesive, a dispensing device such as a pump, a transport device, for example a hose, and an applicator, i.e. nozzle. In certain transformations comprising multiple adhesive bonds for example the process equipment may comprise a reservoir, pump, hose and an application head with one or more applicator nozzles disposed thereon. Alternatively, the transformation may comprise a reservoir, pump, hose and more than one application head with one or more applicator nozzles disposed thereon. It is also anticipated that one reservoir may supply multiple transformations for example of the same adhesive is used for two separate bonding applications the same reservoir may be used to hold the supply of adhesive. Adhesive bonding may comprise one or more of the following transformations, adhesive application, material combining, nipping and/or calendaring.

It is to be appreciated that many forms of bonding may be used to create a bond within a specific element for example bonding two layers of a folded element together or alternatively to attach two or more elements of an absorbent article together. For example, thermal bonding may be used to create such bonds. There are several specific types of thermal bonds including thermal bonds resulting from direct application of heat, thermal bonds generated by sonic waves for example, ultrasonic bonds and pressure bonds which generate heat by means of pressure. A thermal bond may be present in one position on the absorbent article or may be present in laterally or longitudinally opposing pairs. In embodiments wherein laterally or longitudinally opposing pairs of thermal bonds are present the pairs of bonds and the equipment used to create the pairs of bonds may form a transformation. In embodiments comprising multiple thermal bonds for example a continuous pattern of thermal bonds extending the length and/or the width of the absorbent article the equipment used to create such a continuous pattern of thermal bonds may form a transformation.

Although not specifically recited in the process steps shown in FIGS. 8-8B, it is to be appreciated that some process steps may include a transformation referred as activation. The activation of a web of material or a composite web of several materials can provide an activated web material that can be laterally extended beyond its original dimension with the application of relatively less force than that required to extend the same material to the same extent when unactivated. In certain embodiments, the result of activation is the creation of ridges and valleys in one or more layers forming the activated web material. Application of opposing divergent forces directed generally perpendicular to the ridges and valleys typically results in the extension of such a formed web material along an axis between the opposing forces.

The activation approaches described herein may be achieved by using a set, two or more, intermeshing opposing rolls comprising a staggered orientation of teeth such that when a material such a single web or composite web of material passes through the intermeshing rolls, at least a portion of the material is partially deformed to create the desired activation pattern in the web. The teeth of one or more of the rolls may be continuous around the circumference of the roll while the teeth on one or more of the intermeshing opposing rolls may be discontinuous forming intermittent activation (e.g. a structured elastic-like formed web) or a pitched continuous activation (e.g. continuously activated in the opposing waist regions and not the crotch region). One such process for activating materials to provide extensibility is described in U.S. Pat. No. 5,518,801 issued on 21 May 1996 in the name of Chappell et al. The depth to which the teeth intermesh, i.e. depth of engagement, will determine to what degree the web is incrementally stretched and/or plastically deformed and therefore the degree of extensibility imparted to the web. In some embodiments, the absorbent article can be activated in a portion of the backsheet, the waist region, the waistband, the side panels and or the leg cuffs for example, to provide additional extensibility.

In some embodiments, a portion of the absorbent article may be continuously activated meaning that the teeth of two or more of the rolls may be continuous around the circumference of the roll while forming continuous activation (e.g., ring-rolled and thus rendered highly extensible as described in U.S. Pat. No. 5,366,782 (issued Nov. 22, 1994 to Curro, et al)). Specifically, a ring-rolling apparatus which comprises opposing rolls having intermeshing teeth that incrementally stretch and thereby plastically deform the chassis (or a portion thereof) thereby rendering the chassis extensible in the ring-rolled regions. In some embodiments, the side panels that form a portion of at least one of the front and/or back waist regions may be activated by ring rolling while other regions of the absorbent article remain unactivated or are activated to form a structured elastic-like formed web material.

Figure 9:
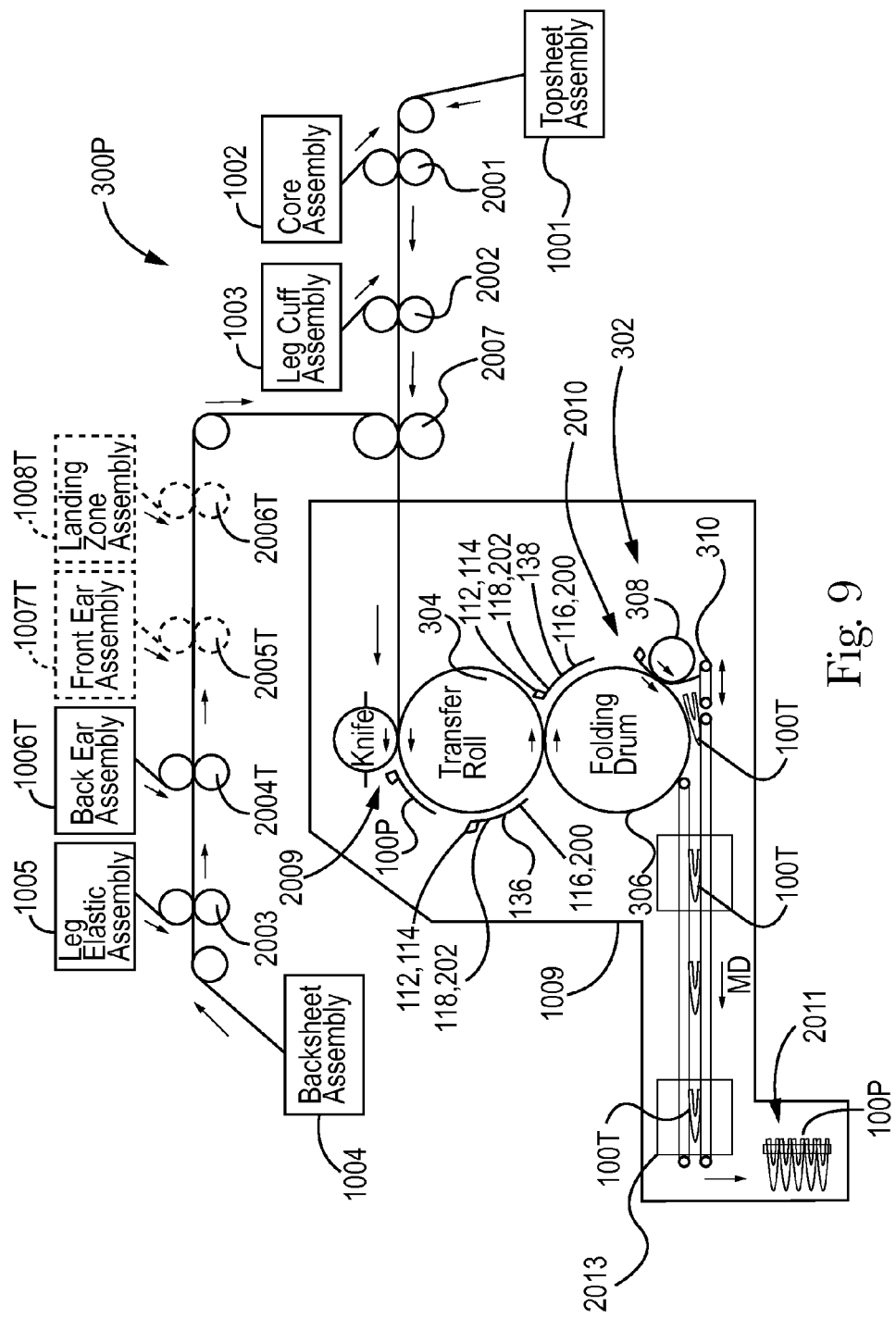
FIG. 9 is a schematic side view of a converting apparatus in a second, pant diaper, configuration adapted to manufacture pant diapers.
Figure 10:
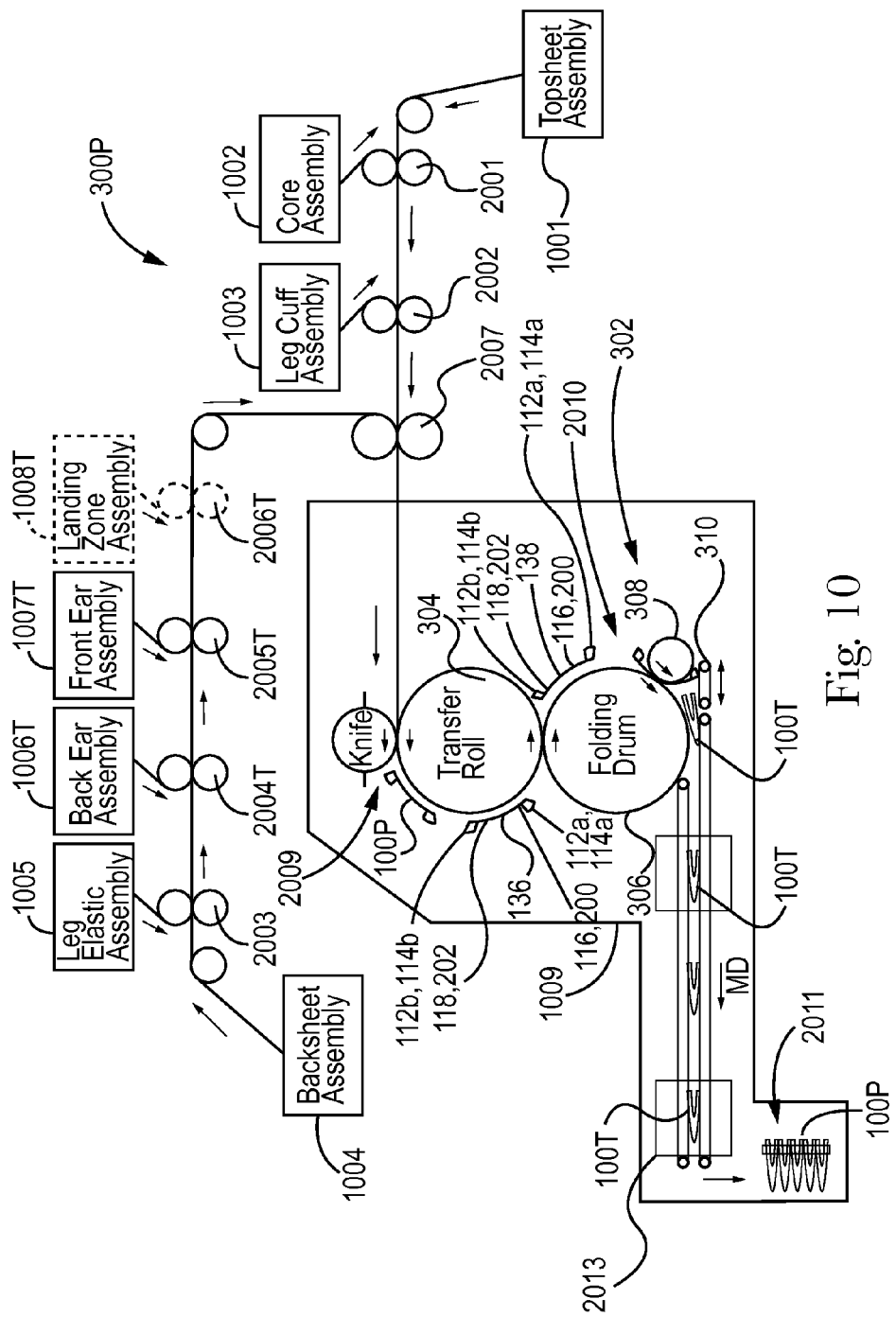
FIG. 10 is a schematic side view of a converting apparatus in a third, pant diaper, configuration adapted to manufacture pant diapers with side seams.

The converting methods and apparatuses herein may include various types of mechanisms to perform the folding transformation 2010 shown in FIG. 8, as well as the folding transformations 2010 discussed below with reference to FIGS. 9 and 10. For example, FIGS. 8-10 show an arrangement that includes a folding apparatus 302 similar to those described in U.S. Patent Publication Nos. 2009/0094941A1 and 2009/0098995A1. The folding transformation herein may also utilize the folding methods and apparatuses described in U.S. patent application Ser. No. 13/051,210 entitled "Apparatuses and Methods for Folding an Absorbent Article," and filed on Mar. 18, 2011.

The method of operation of the folding apparatus 302 may be described with reference to the figures herein and in the context of a method for folding articles, such as taped diapers or pant diapers. The following provides various term explanations that may be useful in understanding the present discussion of the folding apparatus 302. "Leading end portion" means that portion of an absorbent article prior to bi-folding that is disposed forward of the fold line in the machine direction. "Trailing end portion" refers to that portion of an absorbent article prior to bi-folding that is disposed after the fold line in the machine direction. "Fold line" means the portion of an article about which the article is intended to be bi-folded. The fold line typically extends from one longitudinal edge to the other longitudinal edge in the lateral direction. In certain embodiments, the fold line may correspond to the lateral centerline of the article. "Bi-fold" means the leading edge portion and the trailing edge portion of an article on a production line are brought together in a face-to-face configuration along a fold line as the article moves in the machine direction of travel. "Holding an article to the surface of a roll" means employing a holding force to one or more portions of an article in order to join the article at least temporarily to the surface of a roll such that the article is inhibited from traveling in a direction substantially orthogonal to the surface of the roll without reducing or removing the holding force and/or employing a peel-force. This definition is equally applicable to conveyors, e.g., the bi-fold conveyor assembly described herein below. "Peel force" means the force applied to an object in a direction that is substantially perpendicular to the plane of the surface in which the object lies or on which the object rests. A force applied in a direction within 45° of the perpendicular direction may be considered a peel force. "Shear force" means the force applied to an object in a direction that is substantially parallel to the plane of the surface in which the object lies or on which the object rests. A force applied in a direction within 45° of the parallel direction may be considered a shear force.

As shown in FIGS. 8-10, the articles (i.e. taped and pant diapers 100T and 100P) advance in a machine direction and are to be folded along a cross directional fold line. Each article includes a leading end portion 200 that may correspond with the front waist region 116 and a trailing end portion 202 that may correspond with the rear waist region 118. After the final knife cut 2009, the articles are received onto a transfer roll 304, and are subsequently received onto a rotating folding drum 306. It is to be appreciated that some embodiments may not include a transfer roll. For example, in some embodiments, a continuous length of the articles may be received on the folding drum and cut into discrete articles directly thereon. As shown in FIGS. 8-10, the diapers 100T and 100P may be oriented on the outer surface of the folding drum 306 such that the garment facing surface 134, such as defined by the backsheet 136, is engaged with the outer surface of the folding drum. The folding drum 306 is rotated to move the outer surface at a first surface speed and transport the diaper 100T and 100P in the machine direction. A wearer facing surface 132, such as defined by the topsheet 138, of the leading end portion 200 of the diaper 100T and 100P engages an outer surface of a peel roll 308 traveling at the first speed. The leading end portion 200 is transferred from the folding drum 306 to the peel roll 308.

With the leading end portion of the diaper 100T and 100P engaged with the peel roll 308, the trailing end portion 202 of the diaper 100T and 100P remains on the rotating folding drum 306. As the folding drum 306 continues to rotate, clamps from the folding drum may operate to hold diaper 100T and 100P onto the folding drum 306 and the clamped portion of the diaper 100T and 100P continues to move with the folding drum outer surface. When the clamps reach a particular position relative to the peel roll 308, the clamps may exert a force such as, for example, a shear force on the leading end portion 200. The shear force exerted on the leading end portion 200 may be in a direction that is substantially different from or even opposite the direction of travel of the outer surface of the peel roll 308. Thus, the leading end portion 200 may begin to slow down and/or even stop moving. As the leading portion 200 decelerates and/or stops moving, the leading end portion 200 of the diaper 100T and 100P is transferred from the peel roll 308 to a vacuum conveyor 310 including a movable surface. And the movable surface of the vacuum conveyor is accelerated to a surface speed equal to or substantially equal to the surface speed of the folding drum. Next, the garment facing surface 132 of the leading end portion 200 of the diaper 100T and 100P is transferred along the vacuum conveyor and the leading end portion is brought into surface to surface contact with the trailing end portion 202 of the diaper 100T and 100P on the folding drum 306.

It is to be appreciated that the folding apparatus can be configured in accordance with and may include various other features described in U.S. Patent Publication Nos. 2009/0094941A1 and 2009/0098995A1; as well as U.S. patent application Ser. No. 13/051,210, entitled "Apparatuses and Methods for Folding an Absorbent Article," and filed on Mar. 18, 2011.

The converting apparatus 300 is shown in FIG. 8 in a first configuration adapted to manufacture taped diapers 100T. As previously mentioned, the converting apparatus 300 can be placed in a second configuration wherein the transformation mechanisms are arranged to produce a plurality of pant diapers 100P. As such, the second plurality of transformation mechanisms produce a second number of transformations. For example, the converting apparatus 300 is shown in FIG. 9 in a second configuration adapted to produce pant diapers 100P, such as shown and described above with respect to FIGS. 2, 5, and 7. As discussed in more detail below with respect to FIGS. 8 and 9, a relatively large percentage of transformations remain the same in both configurations.

As mentioned above with respect to FIG. 8, it is to be appreciated transformations shown and described in FIG. 9 can be carried out in various different orders than that which is depicted and described herein. As shown in FIG. 9, when the converting apparatus 300 is placed in the second configuration for producing pant diapers 100P, the topsheet assembly process 1001, core assembly 1002, and leg cuff assembly and associated transformations 2001 and 2002 may be the same as discussed above with reference to the taped diaper configuration shown in FIG. 8. In addition, backsheet assembly 1004, leg elastic assembly 1005 and associated transformations 2003 and 2007 shown in FIG. 9 may be the same as discussed above with reference to FIG. 8. As such, the transformations associated with the process assemblies 1001, 1002, 1003, 1004 and 1005 discussed above with reference FIGS. 8A and 8B may also be the same as transformations associated with the process assemblies 1001, 1002, 1003, 1004 and 1005 shown in the pant diaper configuration of FIG. 9.

Although many of the processes and associated transformations may remain unchanged between the taped diaper configuration shown in FIG. 8 and the pant diaper configuration shown in FIG. 9, there are some differences. For example, in FIG. 9, the front ear assembly 1007T and landing zone assembly 1008T as well as associated transformations 2005T and 2006T are shown in dashed lines to indicate these assemblies and transformations may not be used in the pant diaper configuration. In some embodiments of the converting apparatus 300, the transformation mechanisms associated with 1007T, 1008T, 2005T, and 2006T need not be physically removed from the converting apparatus, but rather, simply disabled, "turned-off" or bypassed when the converting mechanism is placed in the pant configuration. It is to be appreciated that in some embodiments, the landing zone assembly 1008T and associated transformation 2006T may be utilized in some pant manufacturing configurations, such as for example, when manufacturing pant diapers 100P having refastenable side panels.

As shown in FIG. 9, the converting apparatus in the second, pant diaper, configuration may include a side panel assembly process 1006P to create side panels 112 and 114, such as shown in FIG. 2. The panels 112 and 114 may also be combined with the backsheet substrate at transformation 2004P. It is to be appreciated that the side panel assembly process 1006P may also include various transformations. For example, the side panel assembly process 1006P may include the identical transformations as discussed above with reference to the back ear assembly process 1006T shown in FIGS. 8 and 8B.

As shown in FIGS. 8 and 9, the final forming process 1009 also may include some different transformations depending on whether the converting apparatus is in the first, taped diaper, configuration or the second, pant diaper, configuration. For example, the ear folding transformation 2008T shown in FIG. 8 is removed or disabled when the converting apparatus 300 is placed in the pant configuration shown in FIG. 9. As such, when the pant diapers 100P in FIG. 9 advance past the final knife transformation 2009, the side panels 112 and 114 may be extended laterally outward from the longitudinal side edges 128 and 130 of the chassis 102, such as shown in FIG. 2. In addition, as shown in FIG. 9, the pant diapers 100P are subject to the same folding transformation 2010 as described with reference to the taped diaper configuration in FIG. 8. As such, the converting apparatus 300 may utilize the same folding apparatus 302, such as described above, whether operating in the taped diaper configuration or the pant diaper configuration. However, when the pant diapers 100P are folded 2010, the side panels 112 and 114 remain in laterally extended positions.

As shown in FIG. 9, the folded pant diapers 100P are subjected to additional transformations not applied to the taped diapers 100T. In particular, the folded pant diapers 100P are subjected to a side panel connection transformation 2012 and may be subjected to a side panel tucking transformation 2013 before advancing to the stacking transformation 2011.

When the folded pant diapers 100P advance from the folding transformation 2010 and through the side panel connection transformation 2012, the distal end regions 176 of the laterally extending side panels 112 and 114 are connected with another portion of the pant diaper 100P. For example, the proximal end regions 174 of the side panels 112 and 114 such as shown in FIG. 2 may be connected with the rear waist region 118 at transformation 2004P discussed above. As such, the side panel connection transformation 2012 of FIG. 9 may be configured to connect the distal end regions 176 of the side panels 112 and 114 with the front waist region 116 of the diaper pant 100P, such as shown in FIG. 5.

Figure 11:
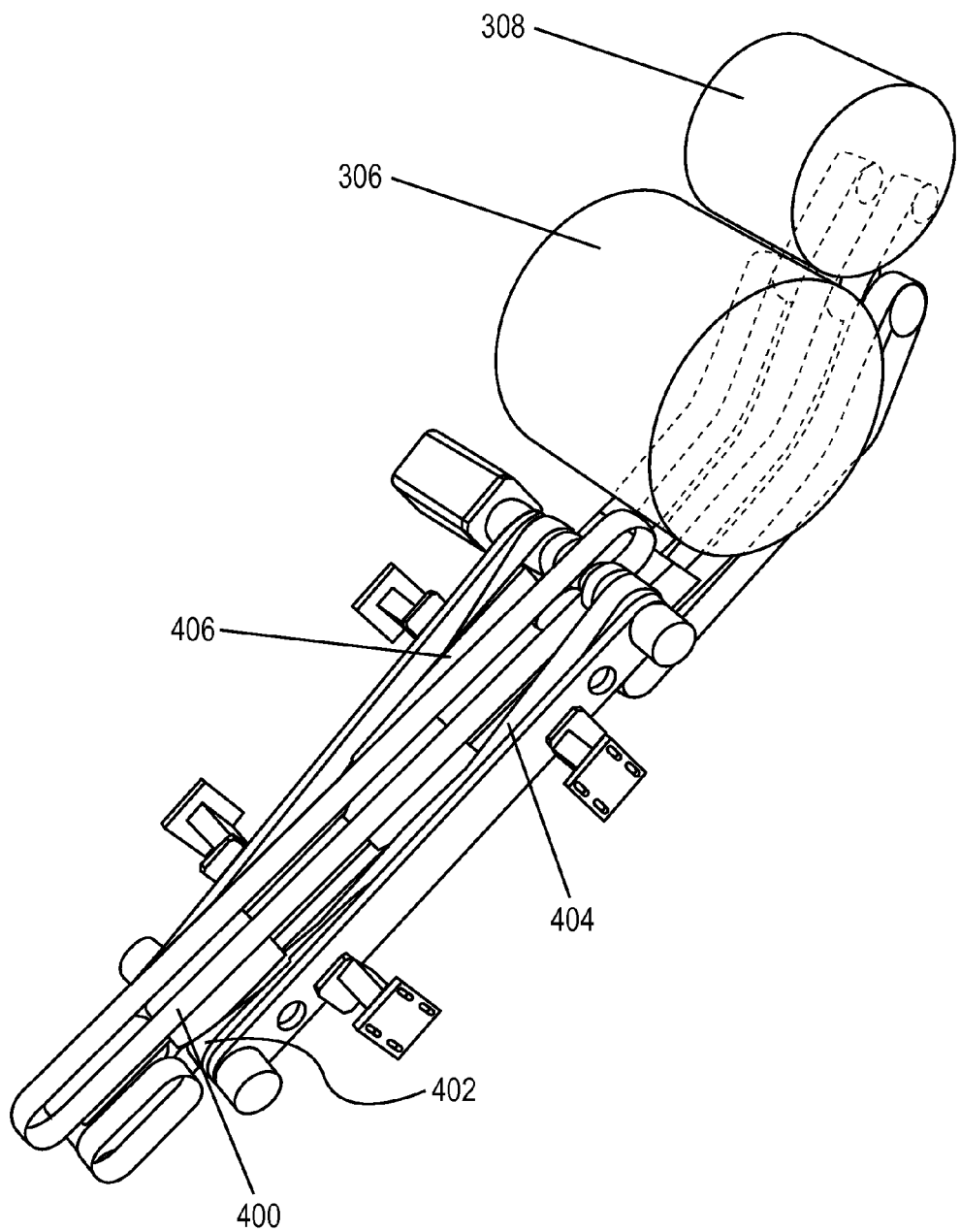
FIG. 11 is a perspective view of a side panel connection apparatus.

It is to be appreciated that various types of transformation mechanisms may be used to carry out the side panel connection 2012. For example, a twisted conveyor arrangement, such as shown in FIG. 11 may used to transport the pant diapers 100P in the machine direction while at the same time bend and fold the side panels 112 and 114 to connect the distal end regions with the front waist region 116 of the chassis 102. As shown FIG. 11, the chassis 100P of the folded pant diapers 100T may be transported in the machine direction away from the folding drum 306 by an upper vacuum conveyor 400 engaged with the rear waist region 118 of the chassis 102 and a lower vacuum conveyor 402 engaged with the front waist region of the 116 of the chassis. First and second twisted vacuum conveyor 404 and 406 may be laterally disposed on opposing sides of the upper and lower vacuum conveyors 400 and 402. In particular, the first and second twisted vacuum conveyors may include a movable surface, such as an endless belt, that twists along the machine direction, MD. As such, the first twisted vacuum conveyor may apply a vacuum force to hold the first side panel 112, and the second twisted vacuum conveyor may apply a vacuum force to hold the second side panel 114 as the pant diaper 100P advances in the machine direction. Thus, as the pant diaper 100P advances, the distal end regions 176 of the side panels 112 and 114 are folded over and placed in contact with the front waist region 116. The distal end regions 176 of the side panels 112 and 114 may also be connected with front waist region 116. As discussed above, the side panels may be refastenably, releasably, or permanently connected with the front waist region in various ways, such as with heat, cohesives, mechanical fasteners, adhesives, and the like.

As shown in FIG. 9, the pant diapers 100P may advance from the side panel connection transformation 2012 to the side panel tucking transformation 2013 before advancing to the stacking transformation 2011. The converting methods and apparatuses herein may include various types of mechanisms to perform the side panel tucking transformation 2012 shown in FIG. 9, as well as the side panel tucking transformation 2012 discussed below with reference to FIG. 10. For example, the side panel tucking transformation 2012 may utilize the tucking methods and apparatuses described in U.S. patent application Ser. No. 13/051,241, entitled "Methods and Apparatuses for Tucking Side Panels of Absorbent Articles," and filed on Mar. 18, 2011; and U.S. patent application Ser. No. 13/051,231, entitled "Methods and Apparatuses for Tucking Side Panels of Absorbent Articles," and filed on Mar. 18, 2011; as well as described in U.S. Pat. Nos. 6,723,035 and 6,776,316.

Figure 7:
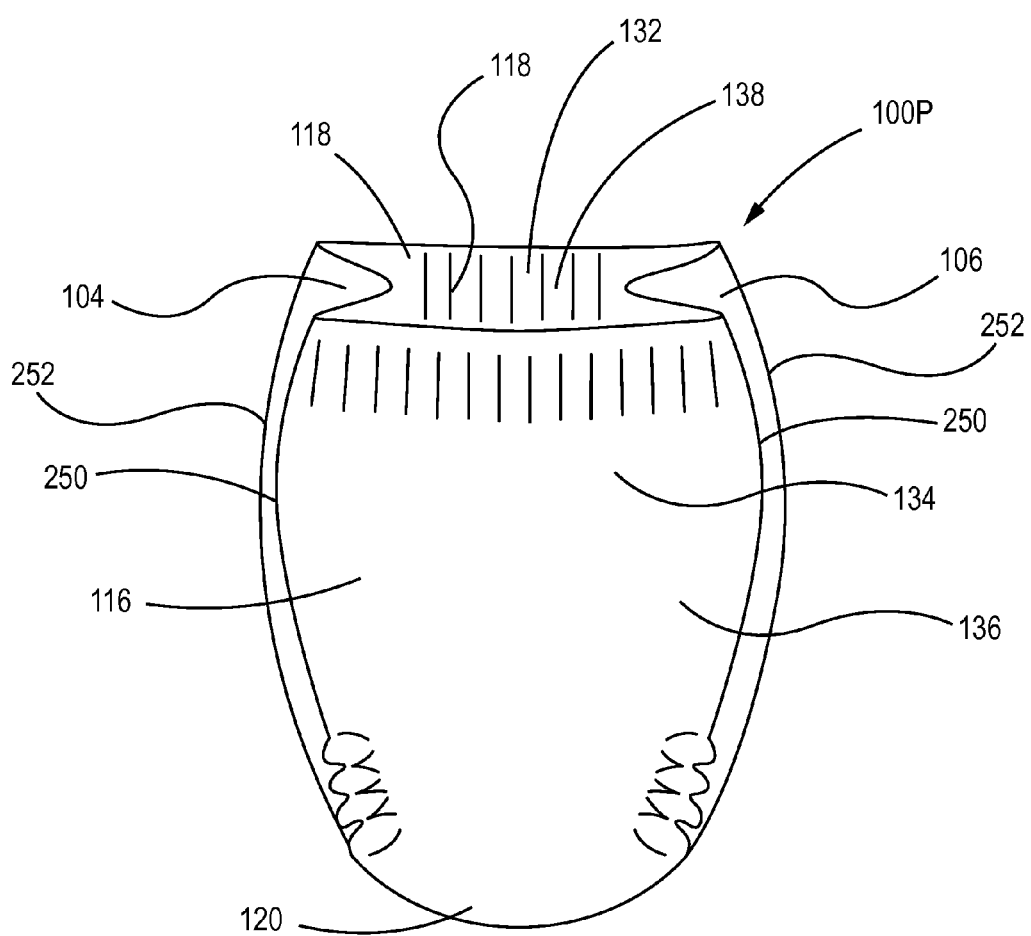
FIG. 7 is a perspective view of a pant diaper with side panels tucked into the interior of a chassis.

FIG. 7 shows the diaper pant 100P with opposing side panels 112 and 114 tucked into the chassis 102. As shown in FIG. 7, portions of each side panel 112 and 114 are inserted into the chassis 102 of the diaper pant 100P such that portions of the side panels are disposed between the interior surface 132 of the front waist region 116 and the rear waist region 118. In addition, the insertion of the side panels 112 and 114 into the chassis 102 defines first longitudinal fold lines 250 along the first waist region 116 and second longitudinal fold lines 252 along the second waist region 118.

FIGS. 12-15 show an example side panel tucking apparatus 500 that may be used to tuck the side panels 112 and 114 into the chassis 102. The apparatus can include 500 a first conveyor 502, a second conveyor 204. Each conveyor 502 and 504 may include a movable surface 506 that may be in the form of a belt wrapped around rollers and configured in an endless loop. One or more of the belts may also be configured as a movable foraminous vacuum conveyor belt that exerts vacuum forces on the chassis 102 to receive, hold, and/or transfer the diaper pant 100P. It is to be appreciated that the each conveyor may include more than conveyor, such as for example, multiple conveyors arranged in series along the machine direction and/or arranged in parallel along the cross direction. In addition, one or more conveyors can be configured as a rotating drum or vacuum drum. The conveyors 202, 204 and 205 advance diaper pants 100P in a machine direction, MD, through a tucking zone represented generally by the side panel tucking transformation 2012 in FIGS. 9 and 10, wherein a side panel tucker pushes the side panels 112 and 114 into the chassis 102.

Figure 12:
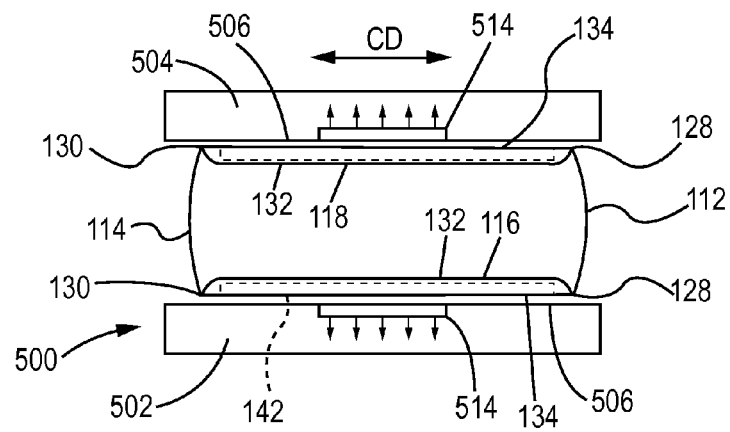
FIG. 12 shows a cross-sectional view of a side panel tucking apparatus and pant diaper.
Figure 13:
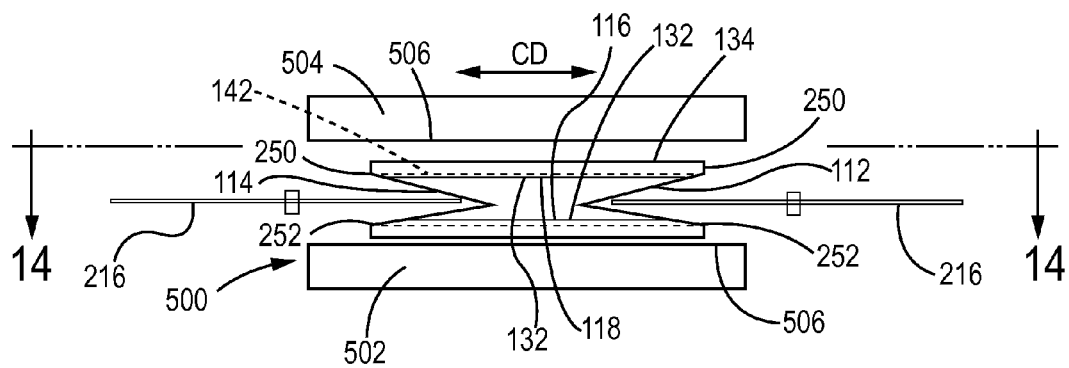
FIG. 13 shows a cross-sectional view of the apparatus and a pant diaper of FIG. 12 with the side panels being tucked.

FIG. 12 shows a cross-sectional view of the diaper pant 100P and first and second conveyors 502 and 504. As shown in FIG. 5, the belt 506 of the first vacuum conveyor 502 includes a vacuum zone 514 that exerts a downward vacuum force on the outer surface 134 of the first waist region 116 of the chassis 102. And the belt 506 of the second vacuum conveyor 504 includes a vacuum zone 514 that exerts an upward vacuum force on the outer surface 134 of the second waist region 118 of the chassis 102. As such, the opposing forces exerted by the vacuum zones 514 on chassis 102 hold the inner surfaces 132 of the first and second waist regions 116, 118 apart. In addition, the side panels 112 and 114 are shown in FIG. 12 in a relatively elongated and untucked configuration.

As shown in FIG. 12, the vacuum zones 514 of the first and second conveyors 502 and 504 each define a lateral or cross directional, CD, width that may be less than the lateral width defined by the opposing longitudinal edges 128 and 130 of the chassis 102. In addition, the lateral or cross directional, CD, width of the vacuum zones 514 may also be less than the lateral width defined by the opposing longitudinal edges of the absorbent core 142. However it is to be appreciated that the vacuum zones may be configured with different lateral widths and may define lateral widths that are larger or smaller than what is depicted. For example, some embodiments may include vacuum zones having lateral widths that are equal to or greater than the lateral widths of the absorbent core and/or chassis. In addition, the conveyors may also be configured with more than one vacuum zone along the cross direction CD and/or machine direction MD.

As the diaper pant 100P advances in the machine direction through the tucking zone, the opposing vacuum forces exerted by the first and second conveyors 502 and 504 may continue to hold the chassis or may be removed from the chassis. And a side panel tucker 516 pushes the side panels 112 and 114 into the chassis 102, such as shown for example in FIG. 13. As the side panels 112 and 114 are pushed into the chassis 102, the inner surfaces 132 of the first waist region 116 and the second waist region 118 may move toward each other. Tucking the side panels 112 and 114 into the chassis 102 also creates longitudinal fold lines 250 and 252 in the chassis 102. In the configuration shown in FIG. 13, the longitudinal fold lines 250 and 252 may also coincide with and may be defined by the longitudinal side edges of the absorbent core 142. It is to be appreciated that the longitudinal fold lines 250 and 252 may be created in various different locations depending on the particular tucking method and configuration. For example, in some embodiments, the longitudinal fold lines may correspond with lateral side edges of the vacuum zones. In some embodiments, the side panels may not be completely tucked inside the chassis, and as such, the longitudinal fold lines may be defined along the lengths of the side panels.

Figure 14:
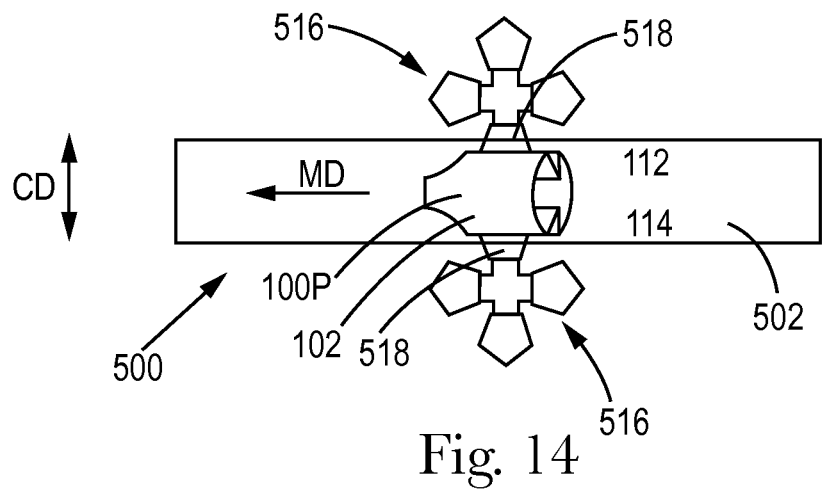
FIG. 14 shows a cross-sectional view of a tucking apparatus utilizing rotating tucker blades and pant diaper of FIG. 13 taken along line 14-14.
Figure 15:
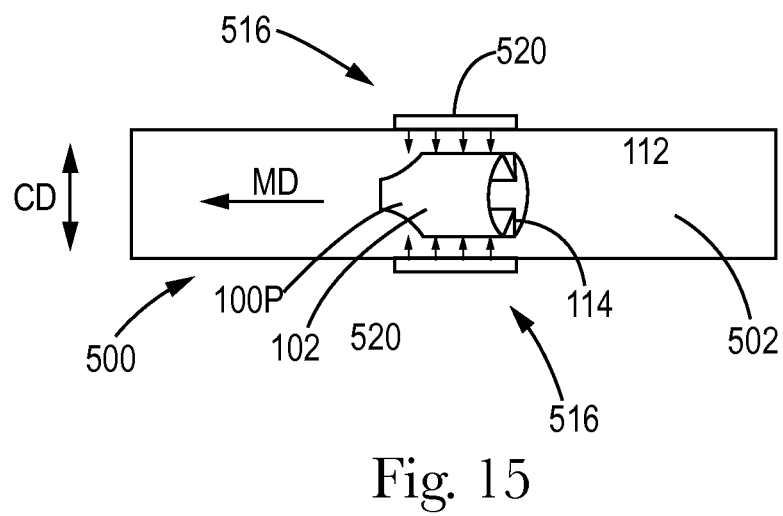
FIG. 15 show a cross-sectional view of a tucking apparatus utilizing air jets and diaper pant of FIG. 13 taken along line 14-14.

It is to be appreciated that side panel tuckers 516 may be configured in various different ways. For example, as shown in FIG. 14, the side panel tuckers 516 are configured as rotating blades 518. As the diaper pant 100P advances in the machine direction past the side panel tuckers 516, a rotating blade or blades may impinge on each of the side panels 112 and 114 and push the side panels into the chassis 102. In another embodiment, shown in FIG. 15, the side panel tuckers 516 are configured as air jets 520. As the diaper pant 100P advances in the machine direction past the side panel tuckers 516, air discharged in the cross direction, CD, from the air jets 520 may impinge on each of the side panels 112 and 114 and push the side panels into the chassis 102. In yet other embodiments, the side panel tuckers 516 may be configured as rails that converge toward each other in the cross direction, CD. The side panel tuckers may be in contact with the absorbent article over the complete machine direction length between the vacuum zone or zones created by the first conveyor 502 and second conveyor 504 through the non-vacuum zone to the vacuum zone or zones created by the first conveyor 502. The side panel tuckers may be oriented in an overlapping orientation with one or more conveyors in the machine direction. Overlapping the side panel tucker and the conveyors may help maintain the side panels in a tucked position until the absorbent article is fully folded, i.e. interior surface 132 in the first waist region 116 is in contact with the interior surface 132 in the second waist region 118. In sill other embodiments, the side panel tuckers may be configured as one of the aforementioned devices that also discharges air to push the side panels into the chassis. For example, the side panel tuckers may be configured to discharge air from rotating blades, blades that travel on tracks, and/or converging rails. Other side panel tucker configurations are disclosed in U.S. Pat. Nos. 6,723,035 and 6,776,316.

Once the side panels 112 and 114 are pushed into the chassis 102, the diaper pant 100P may continue to advance on the first conveyor 502 in the machine direction. The waist regions 116 and 118 of the diaper pant 100P may also be further compressed together to help hold the side panels 112 and 114 in the tucked position, such as with conveyors that converge toward each other in the machine direction.

It is to be appreciated that the converting apparatus can be placed in other configurations to manufacture diaper pants having various other features. For example, FIG. 10 shows the converting apparatus 300 in a third, pant diaper, configuration that may be adapted to produce pant diapers 100P with side seams, such as shown and described above with respect to FIGS. 3, 6, and 7. As discussed above with respect to FIGS. 8 and 9, a relatively large percentage of transformations also remain the same in the taped configurations of FIG. 8 and the pant configuration of FIG. 10.

As mentioned above with respect to FIG. 8, it is to be appreciated transformations shown and described in FIG. 10 can be carried out in various different orders than that which is depicted and described herein. As shown in FIG. 10, when the converting apparatus 300 is placed in the third configuration for producing pant diapers 100P, the topsheet assembly process 1001, core assembly 1002, and leg cuff assembly and associated transformations 2001 and 2002 may be the same as discussed above with reference to the taped diaper configuration shown in FIG. 8. In addition, the backsheet assembly 1004, leg elastic assembly 1005 and associated transformations 2003 and 2007 shown in FIG. 10 may be the same as discussed above with reference to FIG. 8. As such, the transformations associated with the process assemblies 1001, 1002, 1003, 1004 and 1005 discussed above with reference FIGS. 8A and 8B may also be the same as transformations associated with the process assemblies 1001, 1002, 1003, 1004 and 1005 shown in the pant diaper configuration of FIG. 10.

Although many of the processes and associated transformations may remain unchanged between the taped diaper configuration shown in FIG. 8 and the pant diaper configuration shown in FIG. 10, there are some differences. For example, in FIG. 10, the landing zone assembly 1008T and associated transformation 2006T are shown in dashed lines to indicate these assemblies and transformations are not used in the pant diaper configuration. In some embodiments of the converting apparatus 300, the transformation mechanisms associated with 1008T and 2006T need not be physically removed from the converting apparatus, but rather, simply disabled or "turned-off" when the converting mechanism is placed in the pant configuration.

As shown in FIG. 10, the converting apparatus in the second, pant diaper, configuration may include a rear ear panel assembly process 1006P and a front ear panel assembly 1007P to create rear ear panels 112b and 114b and front ear panels 112a and 114a, such as shown in FIG. 3. The rear ear panels 112b and 114b and front ear panels 112a and 114b may also be combined with the backsheet substrate at transformations 2004P and 2005P, respectively. It is to be appreciated that the ear panel assembly processes 1006P and 1007P may also include various transformations. For example, the rear ear panel assembly process 1006P and the front ear panel assembly process may include the identical transformations as discussed above with reference to the back ear assembly process 1006T and front ear assembly process 1007T shown in FIGS. 8 and 8B. In other embodiments, a relatively large ear panel can be added using the transformations of the back ear assembly process 1006T or the front ear assembly process 1007T, wherein the large ear panel is later cut at the final knife 2009 into the back ear panel and the front ear panel.

As discussed above with reference to FIGS. 8 and 9, as shown in FIG. 10, the final forming process 1009 also may include some different transformations depending on whether the converting apparatus is in the first, taped diaper, configuration or the second, pant diaper, configuration. For example, the ear folding transformation 2008T shown in FIG. 8 is removed when the converting apparatus 300 is placed in the pant configuration shown in FIG. 10. As such, when the pant diapers 100P in FIG. 10 advance past the final knife transformation 2009, the front ear panels 112a and 114a and rear ear panels 112b and 114b are extended laterally outward from the longitudinal side edges 128, 130 of the chassis 102, such as shown in FIG. 3. In addition, as shown in FIG. 10, the pant diapers 100P are subject to the same folding transformation 2010 as described with reference to the taped diaper configuration in FIG. 8. As such, the converting apparatus 300 may utilize the same folding apparatus 302, such as described above, whether operating in the taped diaper configuration or the pant diaper configuration shown in FIG. 10. However, when the pant diapers 100P are folded 2010, the front ear panels 112a and 114a and rear ear panels 112b and 114b remain in laterally extended positions.

As shown in FIG. 10, the folded pant diapers 100P are subjected to additional transformations not applied to the taped diapers 100T. In particular, the folded pant diapers 100P are subjected to a side panel connection transformation 2012 and a side panel tucking transformation 2013 before advancing to the stacking transformation 2011. The side panel tucking transformation 2013 and associated mechanisms may the same as discussed above with reference to FIG. 9. However, the side panel connection transformation 2012 in FIG. 10 may have some difference from that discussed above with reference to FIG. 9.

When the folded pant diapers 100P advance from the folding transformation 2010 and through the side panel connection transformation 2012, the distal end regions 176a of the laterally extending front ear panels 112a and 114a are connected with the distal end regions 176b of the rear ear panels 112b and 114b, such as shown for example in FIGS. 3 and 6. As such, the side panel connection transformation 2012 of FIG. 10 may be configured to connect the distal end regions 176a of the front ear panels 112a and 114a with the distal end regions 176b of the rear ear panels 112b and 114b along side seams 178 and 180. It is to be appreciated that various types of transformation mechanisms may be used to carry out the side panel connection 2012 in FIG. 10. For example, the distal end regions 176a and 176b may pass through bonding nips, such as high pressure rolls to refastenably or permanently bond the distal end regions with glue, cohesives, mechanical bonds, ultra-sonic bonds, mechanical fasteners, and the like.

It is to be appreciated that the laterally opposing side seams 178, 180 may be disposed at or adjacent the side edge 128, 130 in one or both waist regions 116, 118. In embodiments wherein the lateral extent of the front waist region 116 is substantially equal to the lateral extent of the back waist region 118 during bonding of the permanent side edge seams 178, 180, the side edge seams may be disposed at or adjacent the side edges of the absorbent article in both the front and back waist regions. In the embodiment, the absorbent article is folded at a laterally extending fold line disposed in the crotch region to bring the front waist region and the back waist region into an interior surface to interior surface face to face orientation. The permanent side edge seams are formed by placing the interior surface of one waist regions in an overlapping relationship with the exterior surface of the opposing waist region adjacent the side edges and subsequently bonding the waist regions together. The first fastening component may be applied to the article prior to forming the permanent side edge seam. The second fastening component may also be applied prior to forming the permanent side edge seam or after forming the permanent side edge seam. In this embodiment, the first fastening component and the non-engagement surface are disposed at least partially within the permanent side edge seam with the fastening surface of the first fastening component in a face to face surface to surface orientation with the non-engagement surface. As removed from the package, the absorbent article is in the form of a pant. The user may apply the absorbent article to the wearer as a pant or alternatively the user may apply the absorbent article as a taped diaper by first releasing the fastening component by separating the front waist region from the back waist region by breaking the permanent side edge seam thereby opening the initial waist opening circumference, then placing the back waist region of the article under the wearer and fastening the first fastening component to the second fastening component to reclose the pant on the wearer.

It is to be appreciated that in some embodiments, the converting apparatus may be configured such that changing from the first, taped diaper, configuration the second (or third), pant diaper, configuration may require the removal, replacement, and/or installation of various transformation mechanisms. Some such mechanisms may be associated with the final forming process 1009. However, in other embodiments, the converting apparatus may be configured with alternate diaper travel paths in the final forming process such that changing from the first, taped diaper, configuration the second (or third), pant diaper, configuration does not require the removal, replacement, and/or installation of various transformation mechanisms associated with the final forming process 1009.

Figure 8C:
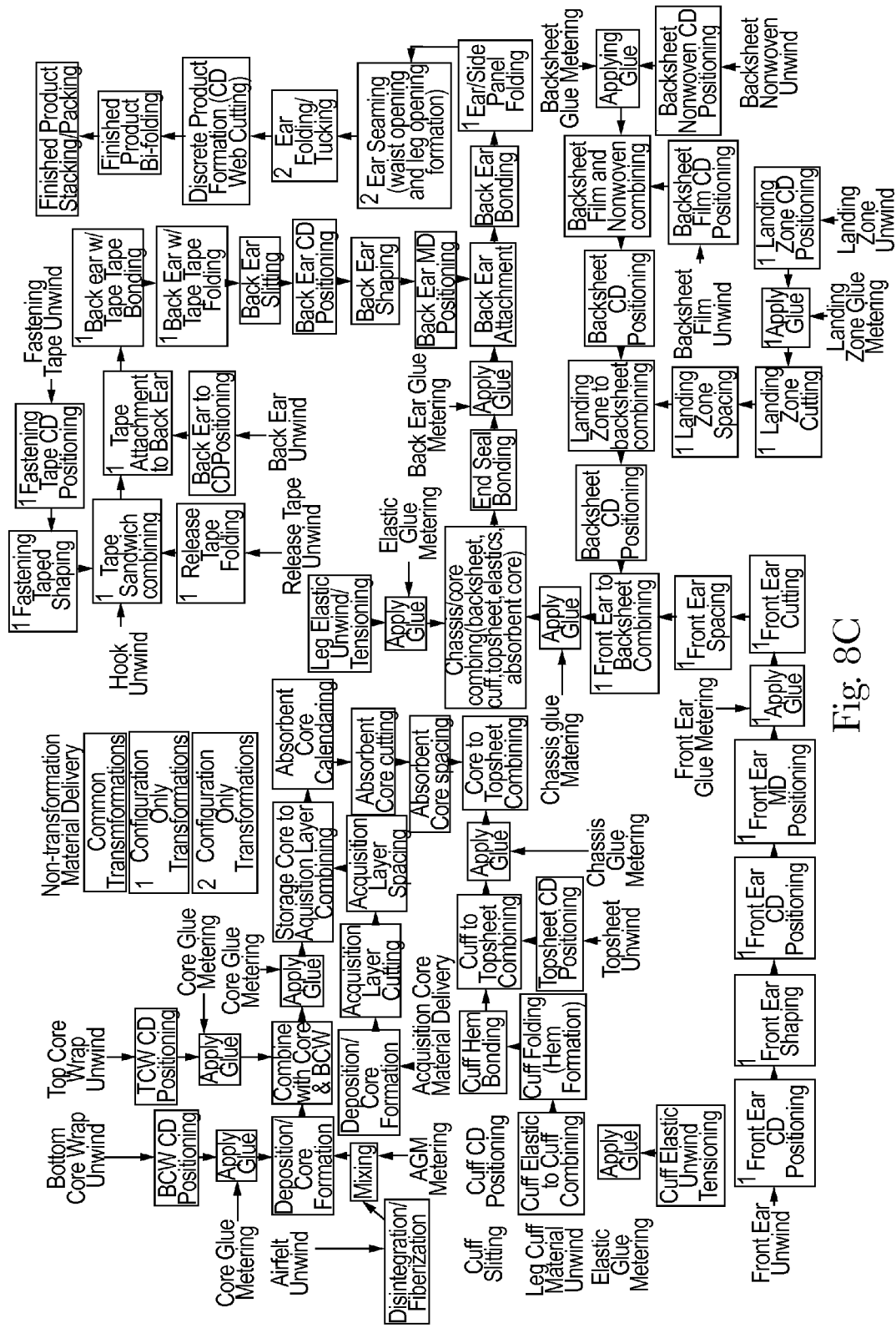
FIG. 8C is an example flow diagram showing various transformations that may be used to construct a taped diaper as well as a pant diaper.

FIG. 8C shows an example flow diagram showing various transformations that may be used to construct a taped diaper as well as a pant diaper. In a first configuration, 70 separate transformations are used to produce a first product, in this example a taped diaper. In a second configuration, 50 separate transformations are used to produce a second product, in this example a pant diaper. Of the 50 transformations utilized in the second configuration, 48 of those transformations, 96%, are the same as the transformations utilized in the first configuration. The plain boxes shown are the transformations that are present in both a first configuration, taped diaper, and a second configuration, pant diaper. The boxes with a 1 are those that are present only in a first configuration, taped diaper, and may be simply turned off or bypassed in the second configuration, pant diaper. The boxes with a 2 are those present in only the second configuration, pant diaper. It is to be appreciated that other converting line arrangements may have a first configuration with a first number of transformations and a second configuration with a second number of transformations, wherein various percentages of the first and second numbers of transformations are the same transformations. For example, in some embodiments, 70% or greater of the second number of transformations used in a second configuration may be the same transformations used in the first configuration. In another example, 80% or greater of the second number of transformations used in a second configuration may be the same transformations used in the first configuration. In yet another example, 90% or greater or even 95% or greater of the second number of transformations used in a second configuration may be the same transformations used in the first configuration.

In order to make two different product types, for example pant diapers and taped diapers, on the same converting line or converting lines comprising similar transformations, it may be important to maintain the line speeds for each of the product types within a specified operating line speed range. The converting lines are typically comprised of multiple transformations each of which may have a centerline defining its optimum operating condition and an operating range around the centerline where the transformation can operate without significant changes or modifications. Therefore, producing both taped and pant products on lines having common transformations requires a specific operating range derived as a function of overall line speed, products per minute. The following ranges have been established for products having a pitch length, length of the product along the longitudinal centerline, of between 480 mm to 550 mm. It should be understood that for a given linear speed the line speed, products per minute, will increase for shorter products and decrease for longer products.

For processes wherein one of the taped or pant diaper products is produced at a first line speed of less than 800 products per minute, the operating line speed range for the other product is defined as the first line speed+/−50%. In other words if a taped diaper is made at 500 products per minute then the pant diaper must be produced at a speed of between 250 products per minute and 750 products per minute. Preferably if the processes wherein one of the taped or pant diaper products is produced at a first line speed of less than 800 products per minute, the operating line speed range for the other product is defined as the first line speed+/−25%. In other words if a taped diaper is made at 600 products per minute then the pant diaper must be produced at a speed of between 450 products per minute and 750 products per minute.

For processes wherein one of the taped or pant diaper products is produced at a first line speed of between 800 and 960 products per minute, the operating line speed range for the other product is defined as the first line speed+/−30%. In other words if a taped diaper is made at 900 products per minute then the pant diaper must be produced at a speed of between 630 products per minute and 1170 products per minute. Preferably if the processes wherein one of the taped or pant diaper products is produced at a first line speed of between 800 and 960 products per minute, the operating line speed range for the other product is defined as the first line speed+/−10%. In other words if a taped diaper is made at 900 products per minute then the pant diaper must be produced at a speed of between 810 products per minute and 990 products per minute.

For processes wherein one of the taped or pant diaper products is produced at a first line speed of greater than 960 products per minute, the operating line speed range for the other product is defined as the first line speed+/−20%. In other words if a taped diaper is made at 1000 products per minute then the pant diaper must be produced at a speed of between 800 products per minute and 1200 products per minute. Preferably if the processes wherein one of the taped or pant diaper products is produced at a first line speed of greater than 960 products per minute, the operating line speed range for the other product is defined as the first line speed+/−5%. In other words if a taped diaper is made at 1000 products per minute then the pant diaper must be produced at a speed of between 950 products per minute and 1050 products per minute.

Maintaining the process or processes within the desired operating line speed range may help minimize the down time to make adjustments between taped and pant products and will maximize the overall efficiency and synergy of the process. In addition, it may help simplify development since each of the multiple transformations needs to only be developed for one type of product and subsequently can be reapplied to the second type of product.

It is to be appreciated that various types of pant and taped diapers may be constructed in accordance with the aforementioned methods and apparatuses. As such, embodiments of such apparatuses and methods may be configured to construct pant and taped diapers having some elements that are configured with specified ranges of performance parameters.

In some embodiments, pant and taped diapers having inner leg cuffs may be constructed in accordance with the above-described methods and apparatuses, wherein the inner leg cuffs are configured to have a range of force characteristics, as described below. In one form, such as shown in FIGS. 16-18, an inner leg cuff may include a rectilinear specimen of a SMS (Spunbond-Meltblown-Spunbond) hydrophobic nonwoven 600 with a basis weight of about 15 g/m$^2$, commonly known as Securon® manufactured by Fiberweb, which is cut with a CD width dimension, A, and a MD length dimension, B, shown in FIG. 16. In some embodiments, A may be 52 mm, and B may be 488 mm, wherein the long axis, B, of the specimen 600 is parallel to the machine direction MD of the nonwoven material, and the short axis, A, of the specimen 600 is parallel to the cross direction CD of the nonwoven material. As shown in FIG. 16, the specimen of nonwoven 600 has a first machine direction edge 602, a second machine direction edge 604, a first cross direction edge 606, and a second cross machine direction edge 608.

As shown in FIG. 17A, adhesive 610 (Bostik H2031) is applied in a spiral pattern at a basis weight of 9.3 g/m² uniformly in an area 612 defined by dimension, C, in the cross direction and by dimension, D, in the machine direction. In some embodiments, dimension C may be 8 mm, and dimension D may be 312 mm. The adhesive area 612 is aligned so that a first longitudinal edge 614 is located in a cross direction distance, E, from the first machine direction edge 602, and a first lateral edge 616 is offset by distance, F, in a machine direction from the first cross machine direction edge 606 as shown in FIG. 17A. In some embodiments, distance E may be 10 mm, and distance F may be 75 mm. The adhesive 610 is applied at a suitable elevated temperature directly to the nonwoven substrate 600 (a mask may be used to obtain the desired adhesive area), or alternatively the adhesive 610 may be applied to silicone-coated release paper and transferred to the nonwoven 600 at room temperature after cutting the appropriate sized piece.

As shown in FIG. 17B, two elastic strands 618 (Invista 680 decitex Lycra T262P) each 135.5 mm long in their relaxed state are stretched uniformly to 488 mm (i.e. 260% extension) and adhesively bonded to the nonwoven 600 parallel to the first machine direction edge 602 of the specimen 600 by pressing the stretched strands 618 onto the specimen. A first elastic strand 618 may be located a distance, G, from the first machine direction edge 602, and the second elastic strand 618 may be located a distance, H, first machine direction edge 602. In some embodiments, distance G may be 11 mm, and distance H may be 13 mm. A ¼" (6.35 mm) wide by 488 mm strip of double sided tape identified as Medical Transfer Adhesive 1524 manufactured by the 3M Company is applied to the specimen 600 so that the nearest edge of the adhesive 620 is parallel to and located distance, J, from the first machine direction edge 602. In some embodiments, distance J may be 2 mm. The second machine direction edge 604 of the nonwoven 600 is lifted and folded over the stretched elastic strands 618 and double sided tape 620 so that a fold line 622 is located a distance, K, from the first machine direction edge 602 as shown in FIG. 17B. In some embodiments, distance K may be 18 mm.

A cross section of the sample is shown in FIG. 18. Using a hand roller, an adequate pressure is applied to the entire specimen to make sure the adhesives 610, 620 bond to the elastics 618 and nonwoven 600. The nonwoven 600 is bonded to the inner surface (e.g. a topsheet) of a diaper having a pitch length of 488 mm so that the cuff spans the entire length of the diaper. The inner cuff may be attached to the inner surface of the diaper 7 mm from any outer cuff or margin, substantially parallel to the longitudinal axis of the diaper, so that the inner cuff is attached along a line 30 mm from the fold line in the inner cuff. The inner leg cuff may be attached to the chassis of a taped or pant diaper by any means known to the art, such as for example, pressure, heat, and ultrasonic bonding.

The inner cuff specimen is tested according to the method for Inner Cuffs in the Cuff Tensile Test described in the Test Methods section below. In one embodiment of an inner cuff specimen that may be applied to a taped or pant diaper, the force value on the $2^{nd}$ unload cycle at 85% extension may be between 0.25 N and 0.45 N and/or the strain value at 0.05 N on the $2^{nd}$ unload cycle may be between 50% and 75%.

In some embodiments, pant and taped diapers having outer leg cuffs may be constructed in accordance with the above-described methods and apparatuses, wherein the outer leg cuffs are configured to have a range of force characteristics, as described below. In one form, such as shown in FIGS. 19-22, an outer leg cuff may include a rectilinear specimen 700 of a SMS (Spunbond-Meltblown-Spunbond) hydrophobic nonwoven with a basis weight of about 15 g/m², commonly known as Securon® manufactured by Fiberweb, is cut with a CD width dimension, L, and a MD length dimension, M, shown in FIG. 19. In some embodiments, dimension L may be 40 mm and dimension M may be 488 mm, so that the long axis, M, of the specimen is parallel to the machine direction MD of the nonwoven material. The specimen of nonwoven 700 has a first machine direction edge 702 and a second machine direction edge 704, a first cross direction edge 706, and a second cross machine direction edge 708, as shown in FIG. 19.

An adhesive 710 (Bostik H2031) is applied in a spiral pattern at a basis weight of 11 g/m² uniformly in an area 712 defined by dimension, N, in the cross direction and by dimension, O, in the machine direction (a mask may be used to obtain the desired adhesive area), or alternatively the adhesive 712 may be applied to silicone-coated release paper and transferred to the nonwoven 700 at room temperature after cutting the appropriate sized piece. In some embodiments, dimension N may be 15 mm, and dimension O may be 276 mm. The adhesive area 712 is aligned so a first longitudinal edge 714 is located a distance, P, from the first machine direction edge 702 of the nonwoven 700 and a first lateral edge 716 is offset a distance, Q, from the first cross direction edge 706, as shown in FIG. 20A. In some embodiments, distance P may be 12.5 mm, and distance Q may be 85 mm. The adhesive 710 is applied at a suitable elevated temperature directly to the nonwoven substrate 700 (a mask may be used to obtain the desired adhesive area), or alternatively the adhesive 710 may be applied to silicone-coated release paper and transferred to the nonwoven at room temperature after cutting the appropriate sized piece. Three elastic strands 718 (Invista 680 decitex Lycra T262P) each 143.5 mm long in their relaxed state are stretched uniformly to 488 mm (i.e. 240% extension) and adhesively bonded to the nonwoven 700 parallel to the machine direction edge 702 of the specimen 700 spaced a distance, R, apart and centered on the nonwoven 700 in the cross direction as seen in FIG. 20B. In some embodiments, distance R may be 3 mm.

Figure 22:
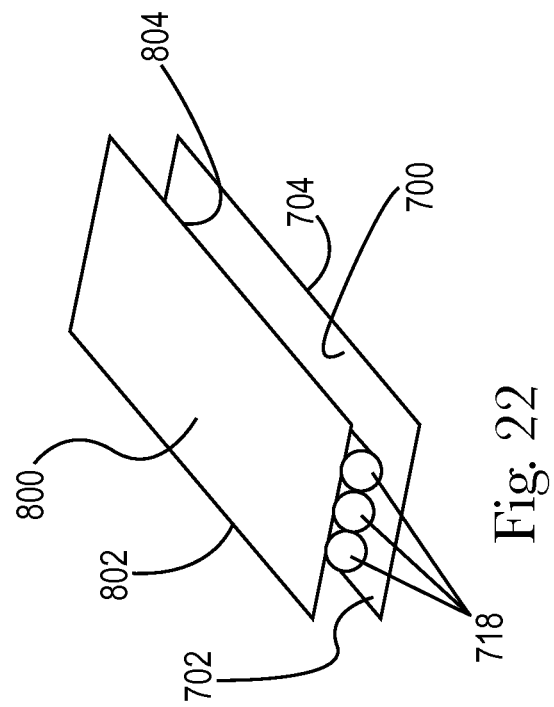
FIG. 22 is an isometric view of an outer cuff specimen.
Figure 21:
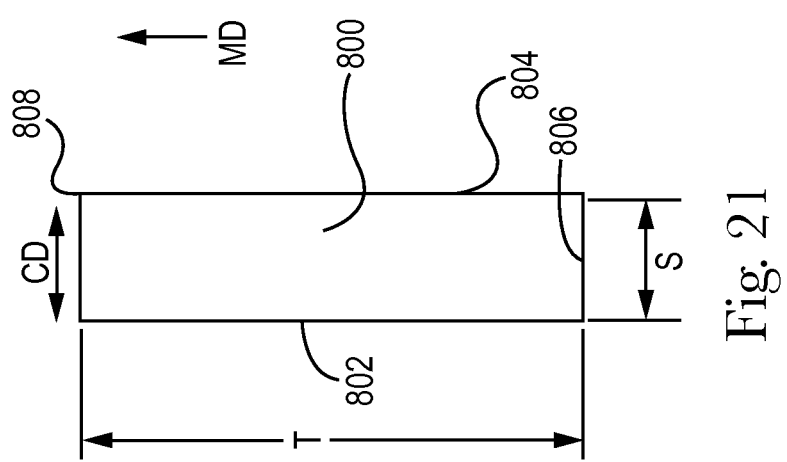
FIG. 21 is a top plan view of a backsheet film specimen for an outer cuff.

A suitable breathable backsheet film 800 layer with a basis weight of 16 g/m² such as a MicroPro™ Microporous Film available through Clopay Plastic Products is cut with a CD width dimension, S, and a MD length dimension, T, shown in FIG. 21. In some embodiments, dimension S may be 40 mm and dimension T may be 488 mm, so that the long axis, T, of the specimen is parallel to the machine direction MD of the backsheet film material. The specimen of backsheet film 800 has a first machine direction edge 802, a second machine direction edge 804, a first cross direction edge 806, and a second cross machine direction edge 808, as shown in FIG. 21. The backsheet film layer 800 is then applied to the assembled elastics 718 and cuff material 700 so that the first machine direction edges 702, 802 and the first cross machine direction edges 706, 806 of the nonwoven 700 and backsheet film 800 are aligned with the stretched elastics 718 between the nonwoven 700 and backsheet film 800, as shown in FIG. 22. Using a hand roller, adequate pressure is applied to the entire sample to make sure the adhesives 710 bond to the elastics 718, nonwoven 700, and backsheet film layers 800.

The outer cuff is tested according to the method for Outer Cuffs in the Cuff Tensile Test described in the Test Methods section below. The force value on the $2^{nd}$ unload cycle at 85% extension may be between 0.35 N and 1.0 N and/or the strain value at 0.05N on the $2^{nd}$ unload cycle may be between 60% and 80%.

In still another form, pant diapers having waist openings may be constructed in accordance with the above-described methods and apparatuses, wherein the waist openings are configured to have a range of force characteristics that may be measured according to the Waist Stretch Test (Pants) recited below. In some embodiments, the waist hoop length at 2000 gf may be between 200 and 800 mm; may be between 500 and 700 mm; and may be from 550 to 670 mm and/or the unload force at a waist hoop length of 530 mm may be between 250 and 2000 gf; may be between 300 and 1500 gf; and may be between 350 and 1150 gf.

In yet another form, taped diapers having back ears may be constructed in accordance with the above-described methods and apparatuses, wherein the back ears are configured to have a range of force characteristics that may be measured according to the Waist Stress-Relaxation Test (Taped Diapers) recited below. In some embodiments, the elongation values at 4N force during the loading cycle may be between 30 mm and 110 mm; may be between 50 mm and 100 mm; and may be between 70 mm and 90 mm. The elongation values at 10N force during the loading cycle may be between 60 mm and 180 mm; may be between 100 mm and 165 mm; and may be between 135 mm and 150 mm. The force at 60 minutes, $F_{60}$, after reaching the maximum elongation as described below according to Step 2 of the Waist Stress-Relaxation Test (Taped Diapers) may be greater than 45% of the maximum force, $F_{max}$, which may be measured at the maximum elongation.

Test Methods Section

Cuff Tensile Test

A suitable tensile tester such as an MTS Alliance with MTS Testworks version 4.0 or equivalent instrument is used. The tester is equipped with grips that are at least as wide as the width of specimens to be tested, lined with one rubber-coated face and one contact line face for both upper and lower grips. A load cell is used so that the maximum load measured is within 10-90% of the maximum capacity of the load cell. The instrument is calibrated according to the manufacturer's specification.

Pitch Length

A disposable product is held in a flat horizontal configuration by tapes or other suitable means. Two cuts are made along the entire length of the product 12.5 mm on either side of the longitudinal centerline. Each straight cut is made vertically through the entire product along its length from the front edge to the rear edge. The central 25 mm wide strip is removed and the topsheet is cut along the transverse centerline. The length of the specimen along the longitudinal centerline is determined to within ±1 mm under minimal tension. This is the measured pitch length of the product. The adjusted pitch length is the measured pitch length minus the combined length of any material held above or below the upper and lower grip lines in the tensile tester, respectively. Thus, if a specimen is mounted in the tensile tester so that 10 mm at each end of the specimen protrudes past the contact line in the clamps, then the adjusted pitch length is the measured pitch length minus 20 mm.

Outer Cuffs:

A disposable product is held in a flat horizontal configuration by tapes or other suitable means. Outer cuff specimens are cut from the product using a sharp blade. The cuts are made parallel to the longitudinal centerline of the product between the inner and outer cuffs so that the specimens contain all of the outer cuff elastics, but none of the inner cuff material. Each straight cut is made vertically through the entire product along its entire length from the front edge to the rear edge, and all material in the specimen in addition to the cuff (including any nonwoven, topsheet, glue, core, backsheet, etc) is retained in the specimen.

Inner Cuffs:

A disposable product is held in a flat horizontal configuration by tapes or other suitable means. Inner cuff specimens are cut from the product using a sharp blade. The entire inner cuffs are cut along the length of the product immediately above the bond joining the cuff to the topsheet, backsheet or other diaper component.

Testing is performed at 23° C.±2° C. and 50%±2% relative humidity.

Test Procedure:

The gauge length is set to enable the specimen to be mounted with minimal slack so that approximately 10 mm at each end of the specimen protrudes past the contact line in the clamp. The load cell must read between 0 and 0.04 N of force after mounting the sample. If the value exceeds 0.04 N, then the gauge length is reduced in 1 mm increments until the force is between 0 and 0.04 N. A 5.0 gram-force pre-load is applied to the specimen using a crosshead speed of 0.5 inches/minute. The adjusted gauge length of the specimen is the distance between the grip lines when the five gram pre-load is reached. The sample is then extended to 95% of the adjusted pitch length at 254 mm/min ($1^{st}$ load cycle), and held at that elongation for 5 seconds. The crosshead is then returned to the adjusted gauge length at 254 mm/min ($1^{st}$ unload cycle) and held for 5 seconds. The sample is again extended to 95% of the adjusted pitch length at 254 mm/min ($2^{nd}$ load cycle), and held at that elongation for 5 seconds. The crosshead is then returned to the adjusted gauge length at 254 mm/min ($2^{nd}$ unload cycle).

Waist Stretch Test (Pants)

Figure 23:
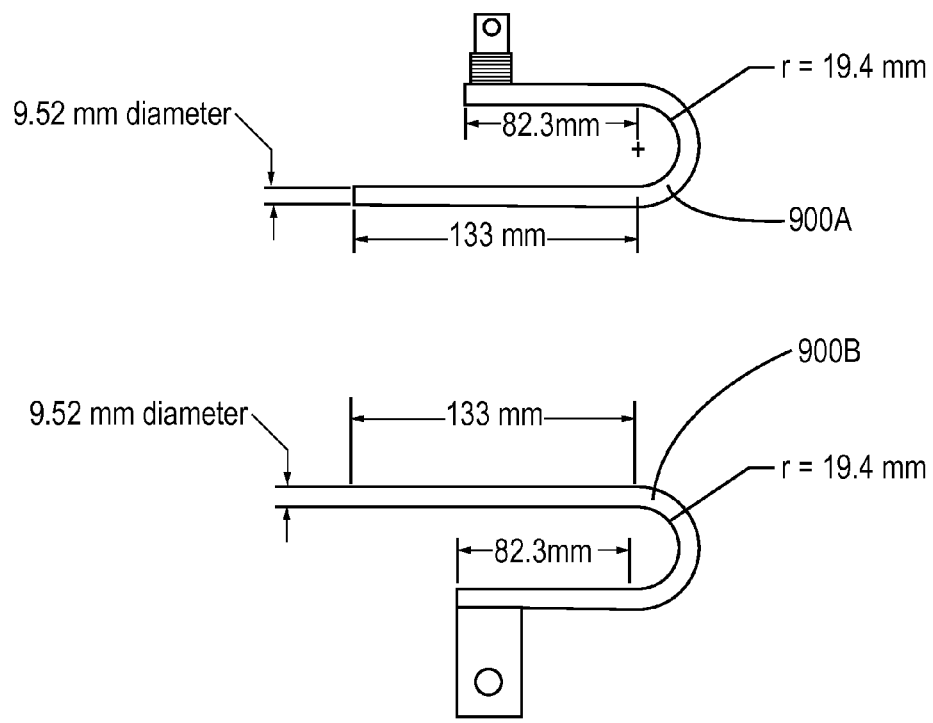
FIG. 23 is a dimensioned view of hook-shaped fixtures used in the waist stretch test (pants) method.
Figure 24:
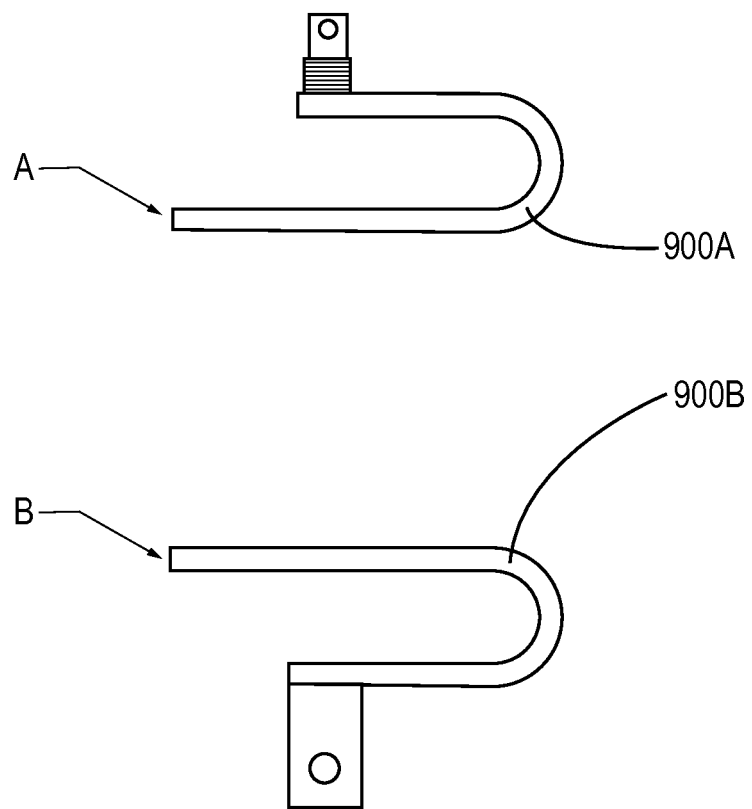
FIG. 24 is a view of the hook-shaped fixtures used in the waist stretch test (pants) method aligned in the same plane.
Figure 25:
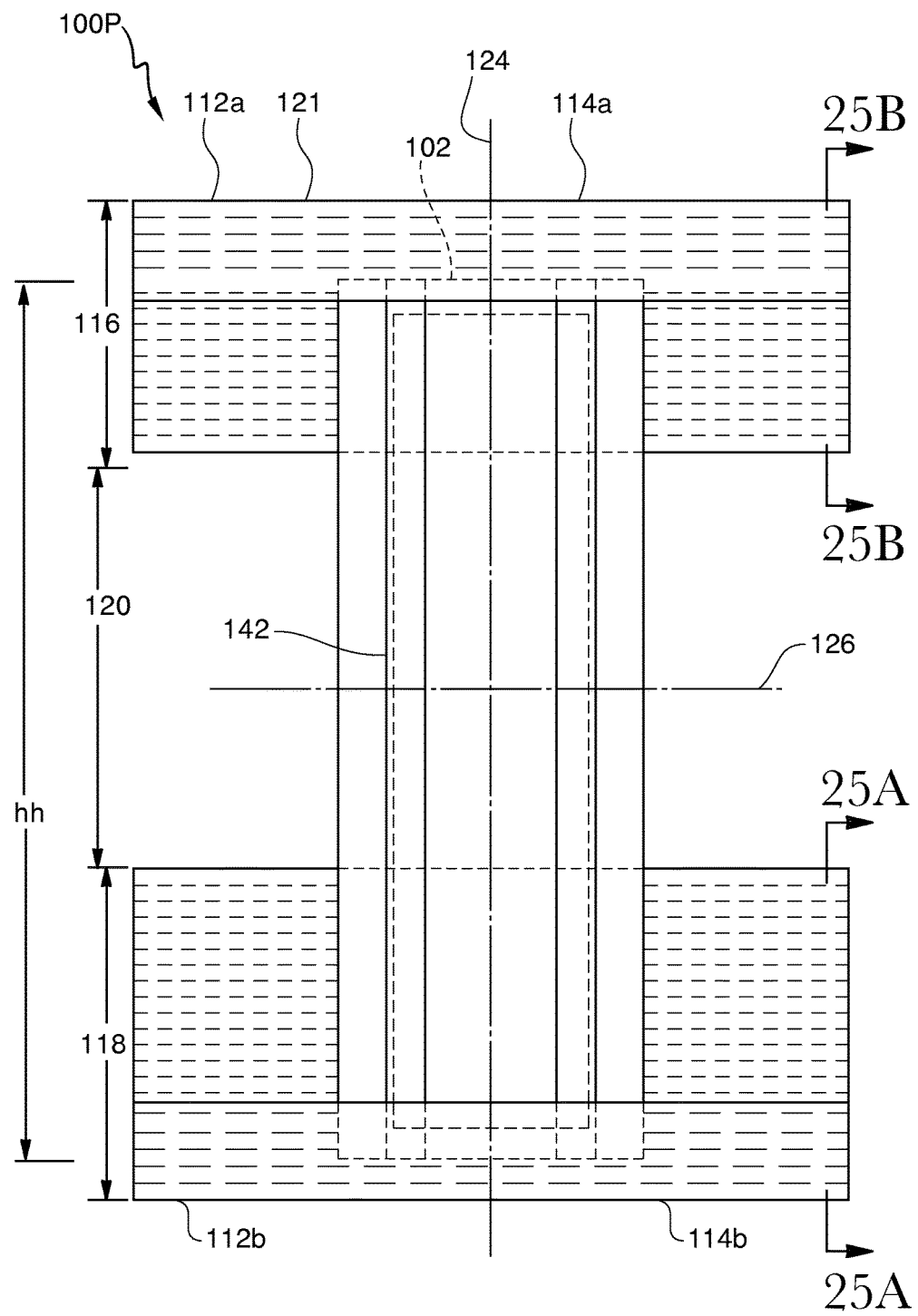
FIG. 25 is a plan view of an exemplary absorbent article laid out flat, suitable in one embodiment of the invention.
Figure 25A:
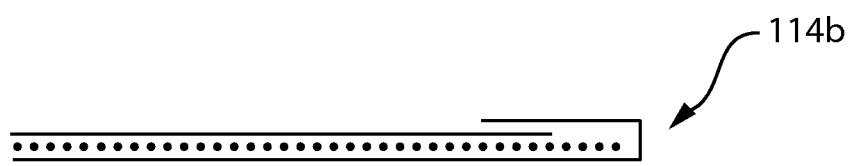
FIG. 25A is a schematic cross section view of a back belt-like flap suitable in one embodiment of the invention, taken along 25A-25A of FIG. 25.
Figure 25B:
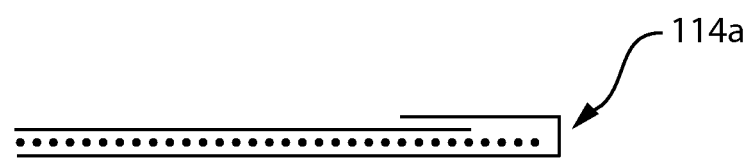
FIG. 25B is a schematic cross section view of a front belt-like flap suitable in one embodiment of the invention, taken along 25B-25B of FIG. 25.
Figure 27:
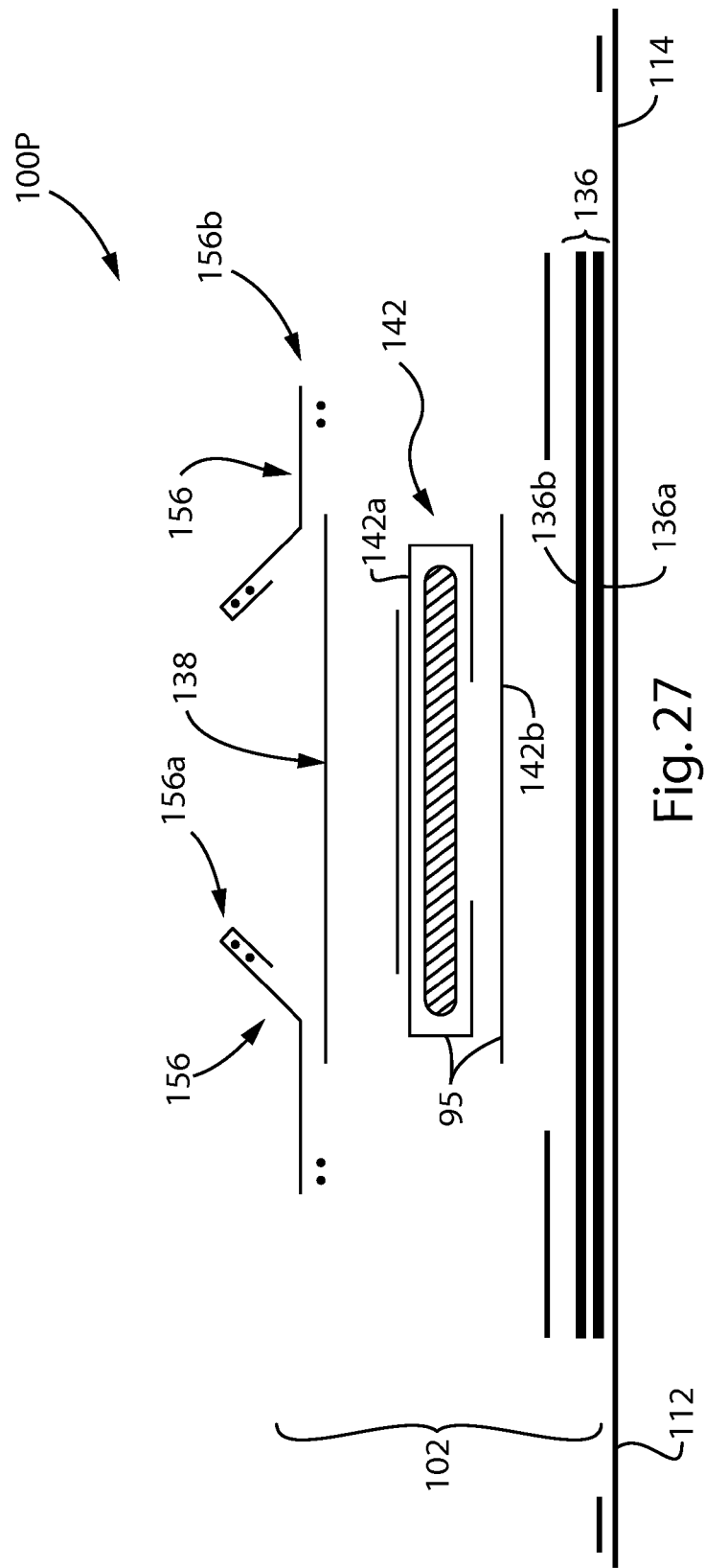
FIG. 27 is a schematic cross section view of an exemplary absorbent article, suitable in one embodiment of the invention.
Figure 28:
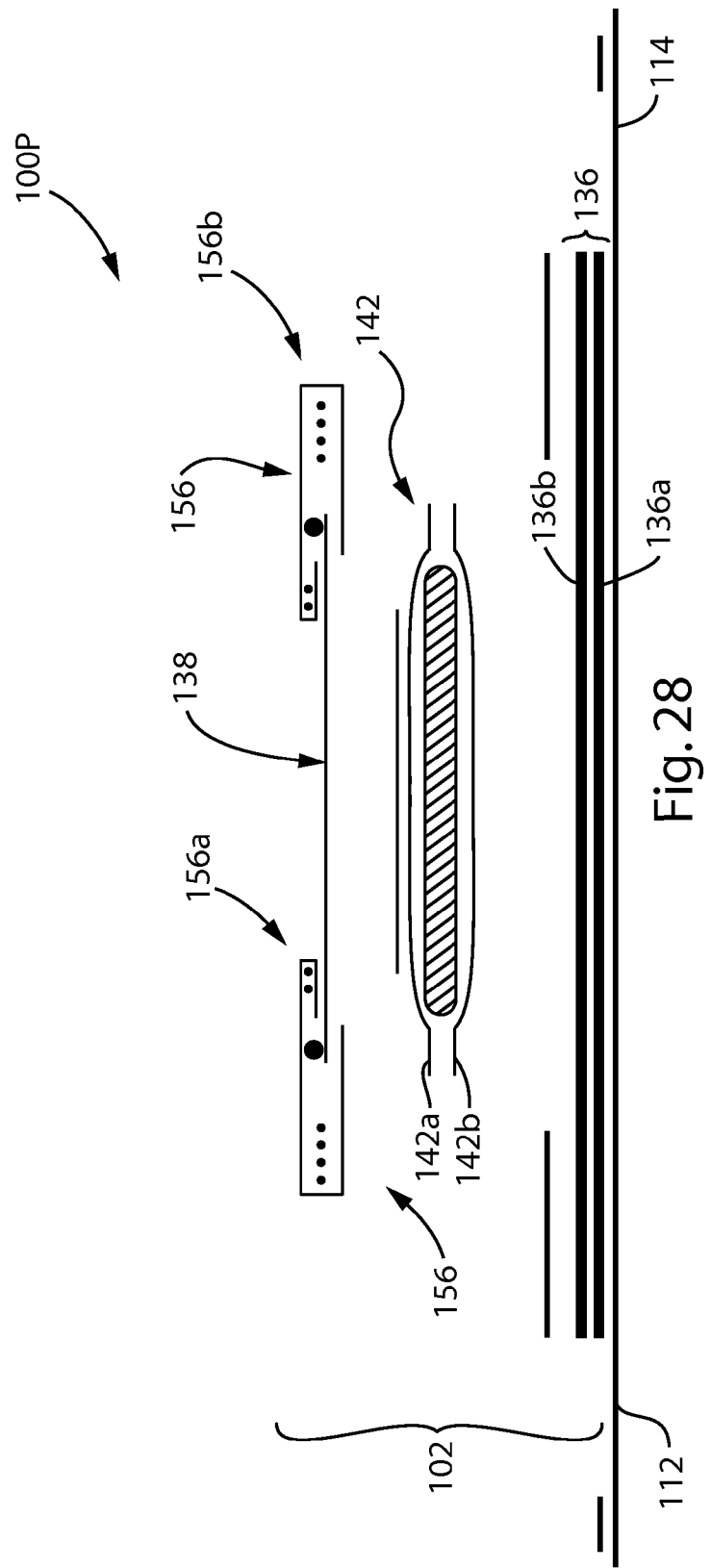
FIG. 28 is a schematic cross section view of an exemplary absorbent article, suitable in one embodiment of the invention.

A suitable tensile tester such as an MTS Alliance with MTS Testworks version 4.0 or equivalent is used. The tester is equipped with hook-shaped fixtures 900A, 900B according to the dimensions specified in FIG. 23. The fixtures 900A, 900B are mounted and aligned on the tensile tester so that the arms A and B as shown in FIG. 24 are horizontal and lie in the same vertical plane. A load cell is used so that the maximum load measured is within 10-90% of the maximum capacity of the load cell. The instrument is calibrated according to the manufacturer's specification. Testing is performed at 23° C.±2° C. and 50%±2% relative humidity.

Test Procedure:

Step 1:

A sample product is removed from its package and carefully opened to avoid stretching any portion of the product. The crosshead of the tensile tester is raised to a point where the product can be mounted on the upper fixture arm by inserting the free end of the arm through the waist opening of the product, and then through a first leg opening, so that the product hangs freely from the upper arm. The product is positioned on the arm so that the side-panel is centered with respect to the vertical axis of the load cell.

The load cell of the instrument is tared with the product hanging freely from the upper arm. The crosshead is then lowered to a point where the lower fixture arm can be inserted through the waist opening of the product and then through the second leg opening without stretching any portion of the product. The product is positioned so that both side panels are centered with respect to the vertical axis of the load cell, and there is no tension in the waist of the product (i.e. there is slack in the waist). The crosshead is then moved up at a speed of 254 mm/min until a load of 2000 gf is obtained (1$^{st}$ cycle load), and the position of the crosshead is recorded. The crosshead is stopped and held for 30 seconds, then returned to its original position at a speed of 254 mm/min (1$^{st}$ cycle unload).

Waist Stress-Relaxation Test (Taped Diapers)

A suitable tensile tester such as an MTS Alliance with MTS Testworks version 4.0 or equivalent instrument is used. The tester is equipped with grips that are at least as wide as the width of specimens to be tested, lined with one rubber-coated face and one contact line face for both upper and lower grips. A load cell is used so that the maximum load measured is within 10-90% of the maximum capacity of the load cell. The instrument is calibrated according to the manufacturer's specification.

Testing is performed at 23° C.±2° C. and 50%±2% relative humidity.

Test Procedure:

Step 1:

A sample product is removed from its package and carefully opened to avoid stretching any of the waist or side-panel materials. The gauge length of the tensile tester is set to 30 mm less than the width of the product at a line bisecting the tape tabs when the product is laid flat without stretching any of the waist or side-panel materials. This is the base gauge length. The tape tabs are opened and each tape is mounted in a separate grip on the tensile tester with the grip line immediately adjacent the bond attaching the tape to the rest of the product.

A 5.0 gram-force pre-load is applied to the sample using a crosshead speed of 0.5 inches/minute. When the five gram pre-load is reached this is the adjusted gauge length. The sample is then immediately extended at a crosshead speed of 508 mm/min [20 in/min] (load cycle) until a force of 15 N is observed. The crosshead is then stopped and returned to the base gauge length at a speed of 508 mm/min (unload cycle), and the sample is removed from the grips. The elongation values at 4 N and 10 N during the load cycle, based on the adjusted gauge length, are recorded.

$\Delta L_{4N}$=(gauge length at 4 N during load cycle)−(adjusted gauge length)

$\Delta L_{10N}$=(gauge length at 10 N during load cycle)−(adjusted gauge length)

Step 2:

A second identical product is removed from its package and carefully opened to avoid stretching any of the waist or side-panel materials. The tape tabs are opened and each tape is mounted in a separate grip on the tensile tester at the base gauge length as described in Step 1 above. The sample is then extended at a crosshead speed of 508 mm/min (load cycle) until the same % elongation is achieved as in Step 1, based on the adjusted gauge length in Step 1. The crosshead is then stopped and held in this position for 60 minutes. The maximum force observed during the Step 2 load cycle ($F_{max}$), and the force at 60 minutes after reaching the maximum % elongation in Step 2 ($F_{60}$) are recorded.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. Disposable absorbent articles constructed using transformations that are at least 70% the same, comprising:
   a taped article in a first package comprising a first chassis, a front waist region and a back waist region, wherein the back waist region comprises laterally opposed ear flaps joined to side edges of the first chassis, wherein proximal side edges of the ear flaps comprise fasteners, wherein the fasteners are not fastened to form a waist opening, such that the taped article is configured as an open diaper in the first package; and wherein the fasteners extend laterally across the laterally opposed ear flaps;
   a pant article in a second package comprising a second chassis, a front waist region and a back waist region, wherein a front belt flap is joined to the front waist region and a back belt flap is joined to the back waist region, and wherein side edges of the front and back belts are joined to form laterally opposed permanent side seams, thus forming a waist opening and leg openings, such that the pant article is configured as a pre-closed diaper in the second package;
   wherein the laterally opposed permanent side seams do not comprise fasteners;
   wherein the first and second chassis are at least identical to the extent that:
      each of the first and second chassis comprise identical chemical compositions of one or more of a topsheet, backsheet film, backsheet nonwoven, core super absorbent polymers, core pulp, core nonwoven, core tissue, leg cuff film, leg cuff nonwoven, super absorbent polymer adhesive, core nonwoven adhesive, leg cuff elastic adhesive, and backsheet nonwoven/film adhesive; and
      each of the first and second chassis comprise the same basis weight of one or more of the topsheet, backsheet film, backsheet nonwoven, core super absorbent polymers, core pulp, leg cuff nonwoven, leg cuff film, super absorbent polymer adhesive, leg cuff adhesive, and backsheet nonwoven/film adhesive;
   wherein the front belt flap comprises a first end edge and a second end edge and a folded edge that forms a portion of the waist opening of the pant article, and wherein the first end edge of the front belt flap is disposed longitudinally outboard of the second end edge of the front belt flap and longitudinally inboard of the folded edge of the front belt flap; and
   wherein the back belt flap comprises a first end edge and a second end edge and a folded edge that forms a portion of the waist opening of the pant article, and wherein the first end edge of the back belt flap is disposed longitudinally outboard of the second end edge of the back belt flap and longitudinally inboard of the folded edge of the back belt flap;

wherein a first portion the first end edge of the front belt flap overlaps the second chassis from a first side edge of the second chassis to a second side edge of the second chassis, and wherein the first portion of the first end edge of the front belt flap is joined to an interior surface of the second chassis, and wherein a second portion of the first end edge of the front belt flap does not overlap the second chassis and is joined to an interior surface of the front belt flap; and wherein the second end edge of the front belt flap overlaps the second chassis from the first side edge of the second chassis to the second side edge of the second chassis and is joined to an exterior surface of the second chassis.

2. The disposable absorbent articles of claim 1, wherein the ear flaps comprise an elastomeric film.

3. The disposable absorbent articles of claim 1, wherein the front and back belt flaps comprise a plurality of elastomeric strands disposed transverse to a longitudinal axis of the pant article.

4. The disposable absorbent articles of claim 3, wherein the front and back belt flaps of the pant article comprise elastomeric film.

5. The disposable absorbent articles of claim 1, wherein the first and second chassis are at least identical to the extent that the first and second chassis have at least one identical component cross sectional order and disposition of a topsheet, backsheet, core, including the core wrap, in at least one the front waist region, back waist region, and crotch region.

6. The disposable absorbent articles of claim 1, wherein the first package comprises indication of a first size, and wherein said second package comprises indication of a second size, wherein said first and second sizes are different.

7. The disposable absorbent articles of claim 6, wherein the first package comprises size X articles and the second package comprises size X+1 articles.

8. The disposable absorbent articles of claim 1, wherein the first package comprises size X articles and the second package comprises size X−1 articles.

9. The disposable absorbent articles of claim 1, wherein each of the first and second chassis comprise absorbent gelling material, and wherein the absorbent gelling material of each are compositionally identical.

10. The disposable absorbent articles of claim 9, wherein the absorbent gelling material of each chassis is adhered to each chassis with compositionally identical adhesive.

11. The disposable absorbent articles of claim 1, wherein the first and second chassis are at least identical to the extent that the first and second chassis have identical component cross disposition of a topsheet, backsheet, core, including the core wrap, in the crotch region.

12. The disposable absorbent articles of claim 1, wherein the first and second chassis are at least identical to the extent that the first and second chassis have identical component cross sectional order and disposition of a topsheet, backsheet, core, including the core wrap, in the front waist region and the back waist region.

13. The disposable absorbent articles of claim 1, wherein the average chassis width of the articles of the first package is substantially the same as the average chassis width of the articles of the second package.

14. The disposable absorbent articles of claim 1, wherein a first portion the first end edge of the back belt flap overlaps the second chassis from the first side edge of the second chassis to the second side edge of the second chassis, and wherein the first portion of the first end edge of the back belt flap is joined to the interior surface of the second chassis, and wherein a second portion of the first end edge of the back belt flap does not overlap the second chassis and is joined to an interior surface of the back belt flap; and wherein the second end edge of the back belt flap overlaps the second chassis from the first side edge of the second chassis to the second side edge of the second chassis and is joined to an exterior surface of the second chassis.

15. The disposable absorbent articles of claim 14, wherein the back belt flap has a greater longitudinal distance at or adjacent to a side seam formed between the front and back belt flap than the longitudinal distance at or adjacent to the side seam of the front belt flap.

16. The disposable absorbent articles of claim 1, wherein the first chassis comprises a waistband disposed inboard of side edges the first chassis, wherein the waistband is discrete from the first chassis.

17. The disposable absorbent articles of claim 1, wherein the backsheets of the first and second articles are substantially the same width.

18. The disposable absorbent articles of claim 1, wherein core wraps of the first and second articles are in the same configuration.

19. The disposable absorbent articles of claim 1, wherein the backsheets of the taped and pant articles have substantially the same moisture vapor transmission rate and hydrohead.

20. The disposable absorbent articles of claim 1, wherein the first and second chassis are at least identical to the extent that each of the first and second chassis comprise identical chemical compositions of each of the topsheet, backsheet film, backsheet nonwoven, core super absorbent polymers, core pulp, core nonwoven, core tissue, leg cuff film, leg cuff nonwoven, super absorbent polymer adhesive, core nonwoven adhesive, leg cuff elastic adhesive, and backsheet nonwoven/film adhesive.

21. The disposable absorbent articles of claim 20, wherein the first and second chassis are at least identical to the extent that each of the first and second chassis comprise the same basis weight of each of the topsheet, backsheet film, backsheet nonwoven, core super absorbent polymers, core pulp, leg cuff nonwoven, leg cuff film, super absorbent polymer adhesive, leg cuff adhesive, and backsheet nonwoven/film adhesive.

22. The disposable absorbent articles of claim 1, wherein the first and second chassis are at least identical to the extent that each of the first and second chassis comprise the same basis weight of each of the topsheet, backsheet film, backsheet nonwoven, core super absorbent polymers, core pulp, leg cuff nonwoven, leg cuff film, super absorbent polymer adhesive, leg cuff adhesive, and backsheet nonwoven/film adhesive.

23. Disposable absorbent articles constructed using transformations that are at least 70% the same, comprising:

a taped article in a first package comprising a first chassis, a front waist region and a back waist region, wherein the back waist region comprises laterally opposed ear flaps joined to side edges of the first chassis, wherein proximal side edges of the ear flaps comprise fasteners, wherein the fasteners are not fastened to form a waist opening, such that the taped article is configured as an open diaper in the first package; and wherein the fasteners extend laterally across the laterally opposed ear flaps;

a pant article in a second package comprising a second chassis, a front waist region and a back waist region, wherein a front belt flap is joined to the front waist region and a back belt flap is joined to the back waist region, and wherein side edges of the front and back belts are joined to form laterally opposed permanent side seams, thus forming a waist opening and leg openings, such that the pant article is configured as a pre-closed diaper in the second package;

wherein the laterally opposed permanent side seams do not comprise fasteners;

wherein the first and second chassis are at least identical to the extent that:

each of the first and second chassis comprise identical chemical compositions of one or more of a topsheet, backsheet film, backsheet nonwoven, core super absorbent polymers, core pulp, core nonwoven, core tissue, leg cuff film, leg cuff nonwoven, super absorbent polymer adhesive, core nonwoven adhesive, leg cuff elastic adhesive, and backsheet nonwoven/film adhesive; and each of the first and second chassis comprise the same basis weight of one or more of the topsheet, backsheet film, backsheet nonwoven, core super absorbent polymers, core pulp, leg cuff nonwoven, leg cuff film, super absorbent polymer adhesive, leg cuff adhesive, and backsheet nonwoven/film adhesive;

wherein the front belt flap comprises a first end edge and a second end edge and a folded edge that forms a portion of the waist opening of the pant article, and wherein the first end edge of the front belt flap is disposed longitudinally outboard of the second end edge of the front belt flap and longitudinally inboard of the folded edge of the front belt flap; and wherein the back belt flap comprises a first end edge and a second end edge and a folded edge that forms a portion of the waist opening of the pant article, and wherein the first end edge of the back belt flap is disposed longitudinally outboard of the second end edge of the back belt flap and longitudinally inboard of the folded edge of the back belt flap;

wherein a first portion the first end edge of the back belt flap overlaps the second chassis from the first side edge of the second chassis to the second side edge of the second chassis, and wherein the first portion of the first end edge of the back belt flap is joined to the interior surface of the second chassis, and wherein a second portion of the first end edge of the back belt flap does not overlap the second chassis and is joined to an interior surface of the back belt flap; and wherein the second end edge of the back belt flap overlaps the second chassis from the first side edge of the second chassis to the second side edge of the second chassis and is joined to an exterior surface of the second chassis.

24. The disposable absorbent articles of claim 23, wherein the first and second chassis are at least identical to the extent that each of the first and second chassis comprise identical chemical compositions of each of the topsheet, backsheet film, backsheet nonwoven, core super absorbent polymers, core pulp, core nonwoven, core tissue, leg cuff film, leg cuff nonwoven, super absorbent polymer adhesive, core nonwoven adhesive, leg cuff elastic adhesive, and backsheet nonwoven/film adhesive.

25. The disposable absorbent articles of claim 24, wherein the first and second chassis are at least identical to the extent that each of the first and second chassis comprise the same basis weight of each of the topsheet, backsheet film, backsheet nonwoven, core super absorbent polymers, core pulp, leg cuff nonwoven, leg cuff film, super absorbent polymer adhesive, leg cuff adhesive, and backsheet nonwoven/film adhesive.

26. The disposable absorbent articles of claim 23, wherein the first and second chassis are at least identical to the extent that each of the first and second chassis comprise the same basis weight of each of the topsheet, backsheet film, backsheet nonwoven, core super absorbent polymers, core pulp, leg cuff nonwoven, leg cuff film, super absorbent polymer adhesive, leg cuff adhesive, and backsheet nonwoven/film adhesive.

* * * * *